United States Patent
Tamamura et al.

(10) Patent No.: US 9,066,983 B2
(45) Date of Patent: Jun. 30, 2015

(54) PEPTIDIC ANTIGEN THAT INDUCES ANTIBODY RECOGNIZING THREE-DIMENSIONAL STRUCTURE OF HIV AND METHOD FOR SYNTHESIZING SAME

(75) Inventors: Hirokazu Tamamura, Tokyo (JP); Toru Nakahara, Nagano (JP); Wataru Nomura, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 49 days.

(21) Appl. No.: 13/319,813

(22) PCT Filed: May 14, 2010

(86) PCT No.: PCT/JP2010/003280
§ 371 (c)(1),
(2), (4) Date: Nov. 10, 2011

(87) PCT Pub. No.: WO2010/134305
PCT Pub. Date: Nov. 25, 2010

(65) Prior Publication Data
US 2012/0052090 A1 Mar. 1, 2012

(30) Foreign Application Priority Data
May 18, 2009 (JP) .................. 2009-120352

(51) Int. Cl.
*A61K 39/385* (2006.01)
*A61K 39/21* (2006.01)
(Continued)

(52) U.S. Cl.
CPC .......... *A61K 47/48253* (2013.01); *A61K 39/00* (2013.01); *A61K 39/21* (2013.01); *C07K 14/005* (2013.01); *C07K 16/1063* (2013.01); *C07K 2317/32* (2013.01); *C12N 2740/16122* (2013.01); *C12N 2740/16134* (2013.01);
(Continued)

(58) Field of Classification Search
None
See application file for complete search history.

(56) References Cited

U.S. PATENT DOCUMENTS

2003/0099935 A1* 5/2003 Chan et al. .................. 435/5
2007/0224212 A1* 9/2007 Bianchi et al. .............. 424/188.1

FOREIGN PATENT DOCUMENTS

JP 2009-080118 A 4/2009
WO WO 2005/118886 A2 12/2005
WO WO 2006/105993 A2 10/2006

OTHER PUBLICATIONS

Tam et al., "A Facile Ligation Approach to Prepare Three-Helix Bundles of HIV Fusion-State Protein Mimetics," Organic Letters, vol. 4, No. 23; pp. 4167-4170 (2002).*

(Continued)

*Primary Examiner* — Zachariah Lucas
*Assistant Examiner* — M. Franco Salvoza
(74) *Attorney, Agent, or Firm* — Hogan Lovells US LLP

(57) ABSTRACT

An object of the present invention is to provide an HIV antibody-inducing peptide antigen that is effective in developing an antibody or a vaccine having specificity and binding activity for the three-dimensional structure of a neutralization target, i.e. the mechanism by which HIV invades a target cell; a method for synthesizing the same; a vaccine comprising the peptide antigen, or an HIV three-dimensional structure-recognizing antibody induced by the peptide antigen; and a preventive and/or therapeutic agent for HIV infection comprising the peptide antigen, the vaccine, or the HIV three-dimensional structure-recognizing antibody as an active ingredient.

8 Claims, 25 Drawing Sheets

(51) Int. Cl.
*A61K 47/48* (2006.01)
*C07K 14/005* (2006.01)
*C07K 16/10* (2006.01)
*A61K 39/00* (2006.01)

(52) U.S. Cl.
CPC . *A61K2039/545* (2013.01); *A61K 2039/55566* (2013.01)

(56) References Cited

OTHER PUBLICATIONS

Olson et al., "Cooperative Helix Stabilization by Complex Arg-Glu Salt Bridges," Proteins: Structure, Function and Genetics 44: pp. 123-132 (2001).*
Nakahara et al., "Remodeling of Dynamic Structures of HIV-1 Envelope Proteins Leads to Synthetic Antigen Molecules Inducing Neutralizing Antibodies," Bioconjugate Chem. 21, pp. 709-714 (2010).*
Sadler et al., "Quaternary Protein Mimetics of gp41 Elicit Neutralizing Antibodies Against HIV Fusion-Active Intermediate State," Peptide Science vol. 90, No. 3, pp. 320-329 (2008).*
Xu et al., "A Template-assembled Model of the N-peptide Helix Bundle from HIV-1 Gp-41 with High Affinity for C-peptide," Chem Biol Drug Des 70: pp. 319-328 (2007).*
AIDS Surveillance Committee, the Ministry of Health, Labor and Welfare, Japan, "Report on Trend of AIDS Incidence," 2008, 6 pages.
Alam, S., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," *J. Immunol.*, 2007, vol. 178, pp. 4424-4435.
Baba, Masanori, "Recent progress of anti-HIV-1 research," *Virus*, 2004, vol. 54, pp. 59-66.
Baba, Masanori, "Advances in antiviral chemotherapy," *Virus*, 2005, vol. 55, pp. 69-76.
Barré-Sinoussi, F., et al., "Isolation of a T-Lymphotropic Retrovirus from a Patient at Risk for Acquired Immune Deficiency Syndrome (AIDS)," *Science*, 1983, vol. 220, pp. 868-871.
Belyakov, I., et al., "Immunobiology of Mucosal HIV Infection and the Basis for Development of a New Generation of Mucosal Aids Vaccines," *Immunity*, 2004, vol. 20, pp. 247-253.
Bewley, C., et al., "Design of a Novel Peptide Inhibitor of HIV Fusion That Disrupts the Internal Trimeric Coiled-coil of gp41," *The Journal of Biological Chemistry*, 2002, vol. 277(18), pp. 14238-14245.
Bianchi, E., et al., "Covalent stabilization of coiled coils of the HIV gp41 N region yields extremely potent and broad inhibitors of viral infection," *PNAS*, 2005, vol. 102(36), pp. 12903-12908.
Cardoso, R., et al., "Broadly Neutralizing Anti-HIV Antibody of 4E10 Recognizes a Helical Conformation of a Highly conserved Fusion-Associated Motif in gp41," *Immunity*, 2005, vol. 22, pp. 163-173.
Carter, C., et al, "Cell Biology of HIV-1 Infection of Macrophages," *Annu. Ref. Macrobiol.*, 2008, vol. 62, pp. 425-443.
Chan, D., et al., "Core Structure of gp41 from the HIV Envelope Glycoprotein," *Cell*, 1997, vol. 89, pp. 263-273.
Conley, A., et al., "Neutralization of divergent human immunodeficiency virus type 1 variants and primary isolates by IAM-41-2F5, an anti-gp41 human monoclonal antibody," *Proc. Natl. Acad. Sci. USA*, 1994, vol. 91, pp. 3348-3352.
Eckert, D., et al., "Inhibiting HIV-1 Entry: Discovery of D-Peptide Inhibitors that Target the gp41 Coiled-Coil Pocket," *Cell*, 1999, vol. 99, pp. 103-115.
Eckert, D., et al., "Mechanisms of Viral Membrane Fusion and Its Inhibition," *Annu. Rev. Biochem.*, 2001, vol. 70, pp. 777-810.
Eckert, D., et al., "Design of potent inhibitors of HIV-1 entry from the gp41 N-peptide region," *PNAS*, 2001, vol. 98(20), pp. 11187-11192.
"Hito Retorovirusu Kenkyu no Saizensen,", *Human Immunodeficiency Virus and Human T-cell Leukemia*, 2002, edited by Naoki Yamamoto, published by Hiromasa Hirano, Springer-Verlag Tokyo, Inc., pp. 9, 13, 14, 16, 73, 74 and 88.

Hewer, R., et al., "Peptide immunogens based on the envelope region of HIV-1 are recognized by HIV-AIDS patient polyclonal antibodies and induce strong humoral immune responses in mice and rabbits," *Molecular Immunology*, 2003, vol. 40, pp. 327-335.
Jiang, S., et al., "A Conformation-Specific Monoclonal Antibody Reacting with Fusion-Active gp41 from the Human Immunodeficiency Virus Type 1 Envelope Glycoprotein," *Journal of Virology*, 1998, pp. 10213-10217.
Joyce, J., et al., "Enhancement of α-Helicity in the HIV-1 Inhibitory Peptide DP'178 Leads to an Increased Affinity for Human Monoclonal Antibody 2F5 but Does Not Elicit Neutralizing Responses in Vitro," *The Journal of Biological Chemistry*, 2002, vol. 277(48), pp. 45811-45820.
Kilby, J., et al., "Novel Therapies Based on Mechanisms of HIV-1 Cell Entry," *The New England Journal of Medicine*, 2003, vol. 348, pp. 2228-22238.
Kilby, J., et al., "Potent suppression of HIV-1 replication in humans by T-20, a peptide inhibitor of gp41-mediated virus entry," *Nature Medicine*, 1998, vol. 4(11), pp. 1302-1307.
Koyanagi, Yoshio, "Outline of the HIV Replication and its Cellular Factors: The Track of an Invader in Cell," *Virus*, 2005, vol. 55, pp. 251-258.
Kwong, P., et al., "Structure of an HIV gp 120 envelope glycoprotein in complex with the CD4 receptor and a neutralizing human antibody," *Nature*, 1998, vol. 393, pp. 648-659.
Lalezari, J., et al., "Enfuvirtide, an HIV-1 Fusion Inhibitor, for Drug-Resistant HIV Infection in North and South America," 2003, *N. Engl. J. Med.*, 2003, vol. 348, pp. 2175-2185.
Liu, S., et al., "Different from the HIV Fusion Inhibitor C34, the Anti-HIV Drug Fuzeon (T-20) Inhibits HIV1 Entry by Targeting Multiple Sites in gp-41 and g120," 2005, *The Journal of Biological Chemistry*, vol. 280(12), pp. 11259-11273.
Louis, J., et al., "Covalent Trimers of the Internal N-terminal Trimeric Coiled-coil of gp41 and Antibodies Directed against Them Are Potent Inhibitors of HIV Envelope-mediated Cell Fusion," *The Journal of Biological Chemistry*, 2003, vol. 278(22), pp. 20278-20285.
Lu, M., et al., "A trimeric structural domain of the HIV-1 transmembrane glycoprotein," *nature structural biology*, 1995, vol. 2(12), 1075-1082.
Malashkevich, V., et al., "Crystal structure of the simian immunodeficiency virus (SIV) gp41 core: Conserved helical interactions underlie the broad inhibitory activity of gp41 peptides," *Proc. Natl. Acad. Sci. USA*, 1998, vol. 95, pp. 9134-9139.
Masuda, Takao, "Host factors that regulate the intercellular dynamics of HIV-1 genome during the early phase of infection," *Virus*, 2006, vol. 1, pp. 41-50.
Münch, J., et al., "Discovery and Optimization of a Natural HIV-1 Entry Inhibitor Targeting the gp41 Fusion Peptide," *Cell*, 2007, vol. 129, pp. 263-275.
Nelson, J., et al., "An Affinity-Enhanced Neutralizing Antibody against the Membrane-Proximal External Region of Human Immunodeficiency Virus Type 1 gp41 Recognizes an Epitope between Those of 2F5 and 4E10," *Journal of Virology*, 2007, vol. 81(8), pp. 4033-4043.
Otaka, A., et al., "Remodeling of gp-41-C34 Peptide Leads to Highly Effective Inhibitors of the Fusion of HIV-1 with Target Cells," *Angew. Chem. Int. Ed.*, 2002, vol. 16, pp. 2937-2940.
Ofek, G., et al., "Structure and Mechanistic Analysis of the Anti-Human Immunodeficiency Virus Type 1 Antibody 2F5 in Complex with Its gp41 Epitope," *Journal of Virology*, 2004, vol. 78(19), pp. 10724-10737.
Pantophlet, R., et al., "Fine Mapping of the Interaction of Neutralizing and Nonneutralizing Monoclonal Antibodies with the CD4 Binding Site of Human Immunodeficiency Virus Type 1 gp120," *Journal of Virology*, 2003, pp. 642-658.
Qiao, Z., et al., "Design, Expression, and Immunogenicity of a Soluble HIV Trimeric Envelope Fragment Adopting a Prefusion gp41 Configuration," *The Journal of Biological Chemistry*, 2005, vol. 280(24), pp. 23138-23146.
Root, M., et al., "Protein Design of an HIV-1 Entry Inhibitor," *Science*, 2001, vol. 291, pp. 884-888.
Sato, H., et al., "RNA viruses and mutations," *Virus*, 2005, vol. 55, pp. 221-230.

(56) References Cited

OTHER PUBLICATIONS

Tamamura, Hirokazu, "Research on Production of Specific Antibodies Recognizing Dynamic Supermolecule Mechanisms of HIV Invasion," Ministry of Health, Labor and Welfare Grants-in-Aid for Scientific Research (The Foundation for AIDS Research) Cooperative Research Report, Tokyo Medical and dental University, 2008, pp.

Tan, K., et al., "Atomic structure of a thermostable subdomain of HIV-1 gp41," *Proc. Natl. Acad. Sci. USA*, 1997, vol. 94, pp. 12303-12308.

Trkola, A., et al., "Human Monoclonal Antibody 2G12 Defines a Distinctive Neutralization Epitope on the gp120 Glycoprotein of Human Immunodeficiency Virus Type 1," *Journal of Virology* 1996, vol. 70(2), pp. 1100-1108.

Weissenhorn, W., et al., "Atomic structure of the ectodomain from HIV-1 gp41," *Nature*, 1997, vol. 387, pp. 426-430.

Welch, B., et al., "Potent D-peptide inhibitors of HVI-1 entry," *PNAS*, 2007, vol. 104(43), pp. 16828-16833.

"World Health Statistics 2008," World Health Organization, 2008, pp. 13-14.

Yuki, Y., et al., "Progress towards an AIDS mucosal vaccine," *Tuberculosis*, 2007, vol. 87, pp. S35-S44.

International Preliminary Report on Patentability for PCT/JP2010/003280; date of mailing Dec. 22, 2011 (7 pages).

A. Szczepanska et al., "Synthesis and Conformational Analysis of Novel Trimeric Maleimide Cross-Linking Reagents," Journal of Organic Chemistry, vol. 72, No. 18, Apr. 8, 2007 pp. 6776-6785.

T. Nakahara et al., "Remodeling of Dynamic Structures of HIV-1 Envelope Proteins Leads to Synthetic Antigen Molecules Inducing Neutralizing Antibodies," Bioconjugate Chemistry, vol. 21, Jan. 4, 2010 pp. 709-714.

Supplementary European Search Report dated May 14, 2013, Corresponding to Application No. 10 777 543.9.

\* cited by examiner

Fig. 7
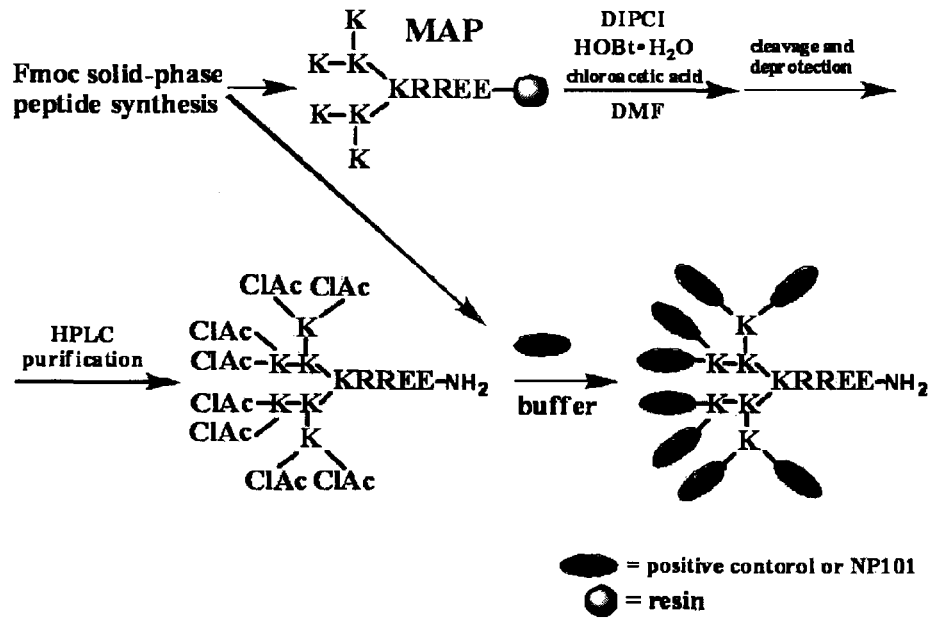
Fig. 8
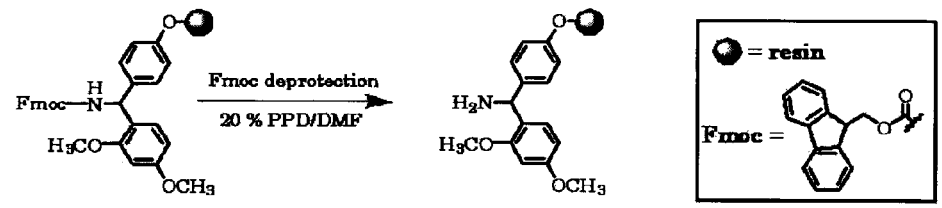
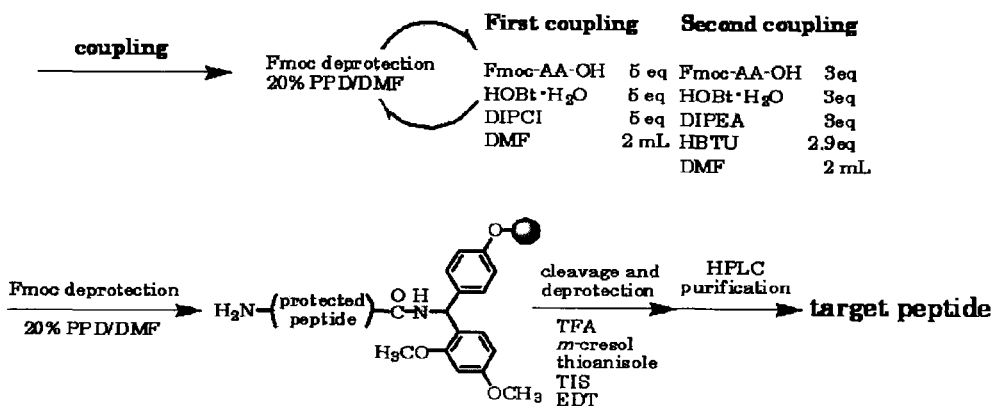

Fig. 11
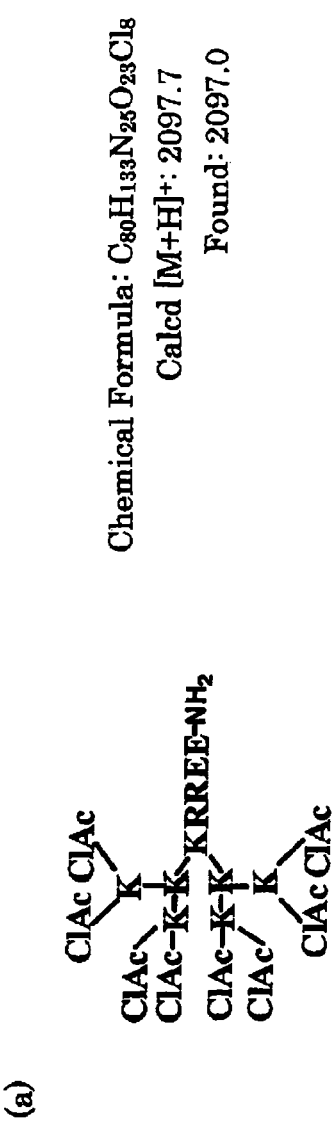
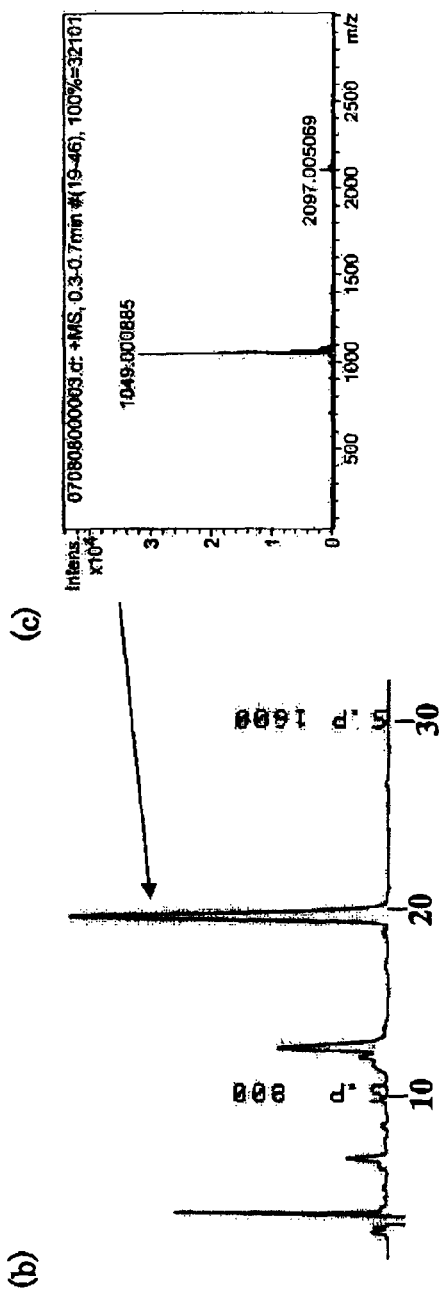

A = Immunization
B = Collection of blood

Fig. 17
(a)
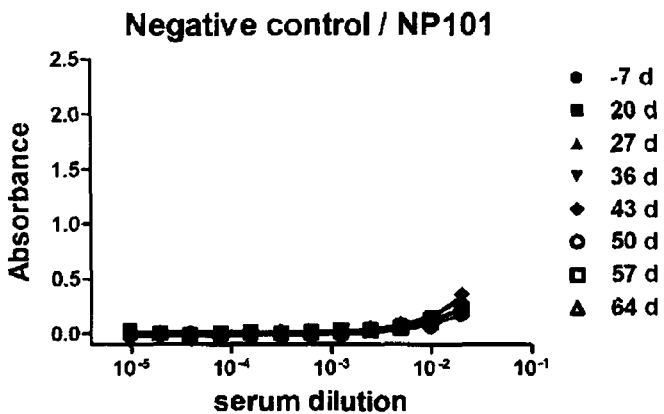
(b)
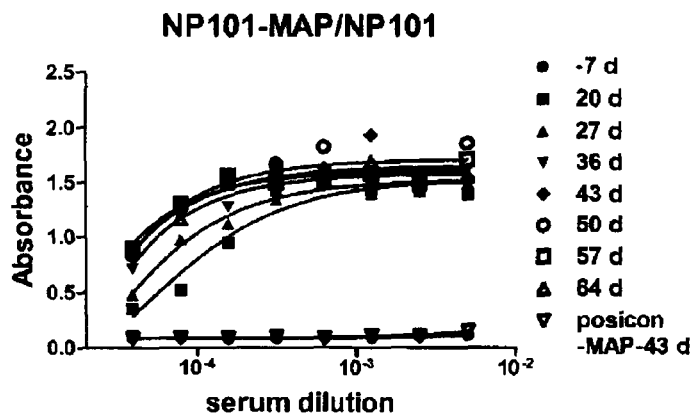
(c)
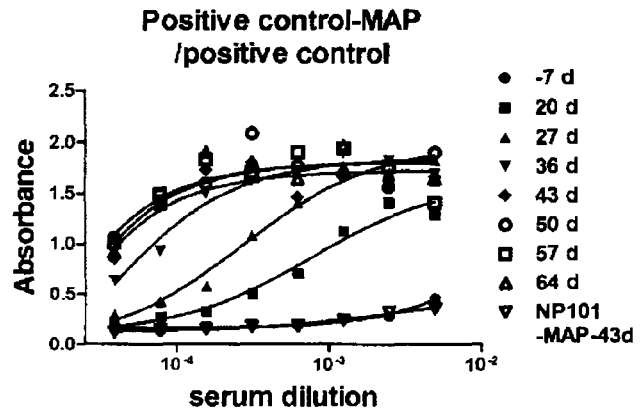

Fig. 27

| compound | retention time | Chemical formula | calcd[M+H]+ | found |
|---|---|---|---|---|
| NP103 | 16.4 min | C222H377N74O64S | 5138.8 | 5137.8 |
| Disulfide dimer | - | C444H751N148O128S2 | 10274.7 | - |
| Monosubstituted | - | C246H411N78O75S | 5693.4 | - |
| Disubstituted | 28.1 min | C468H785N152O138S2 | 10813.3 | 10813.5 |
| NP104 (Trimer) | 34.2 min | C690H1159N226O201S3 | 15933.1 | 15933.8 |

Fig. 28

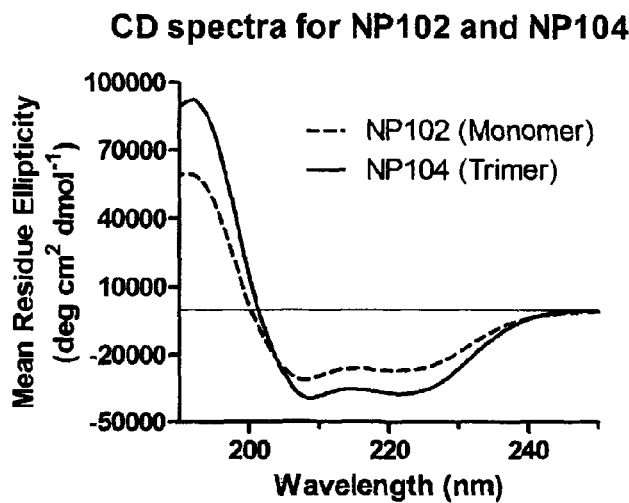

Fig. 29

| peptide | $[\theta]_{222}$[a] | $[\theta]_{222}/[\theta]_{208}$[b] | α-Helicity[c] |
|---|---|---|---|
| NP102 (Monomer) | -30957 | 0.87 | 73% |
| NP104 (Trimer) | -38998 | 0.96 | 95% |

[a] Molar ellipticity (deg cm² dmol⁻¹) of peptides at 222nm
[b] $[\theta]_{222}/[\theta]_{208}$ is the ratio of ellipticity at 222 nm to ellipticity at 208 nm.
[c] The α-helix content was calculated from the ratio of the observed $[\theta]_{222}$ value divided by the predicted molar ellipticity.

Fig. 30
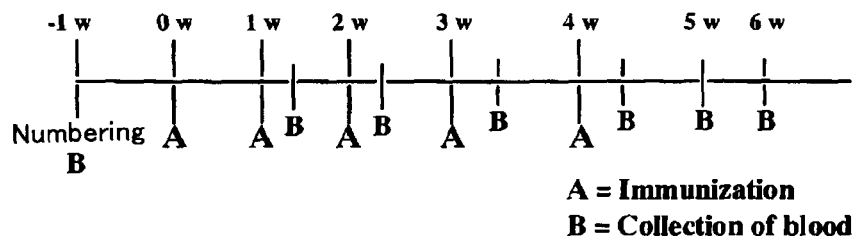
A = Immunization
B = Collection of blood
Fig. 31
(a)
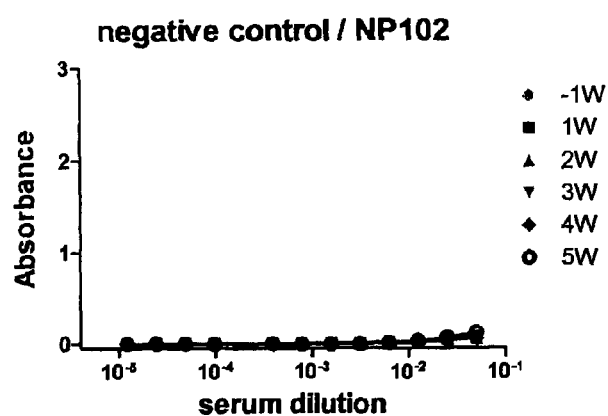
(b)
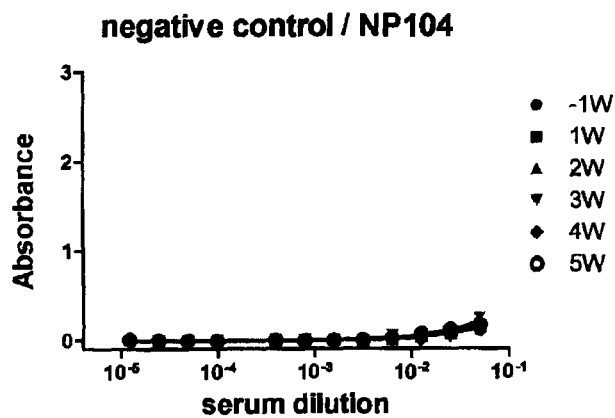

Fig. 32
(a)
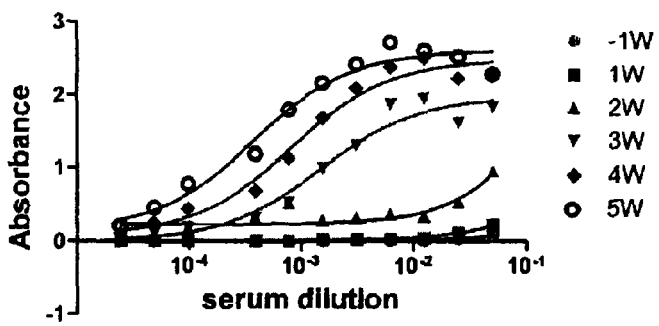
NP102 (both) / NP102
(b)
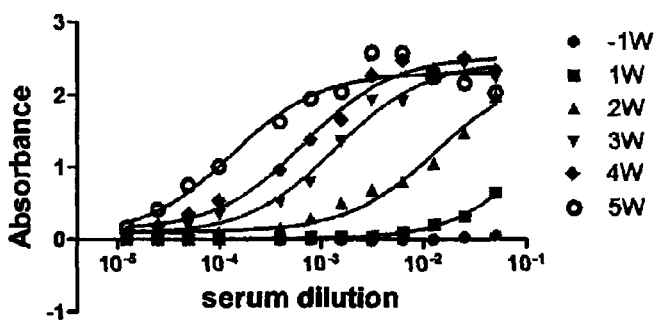
NP104 (left) / NP104
(c)
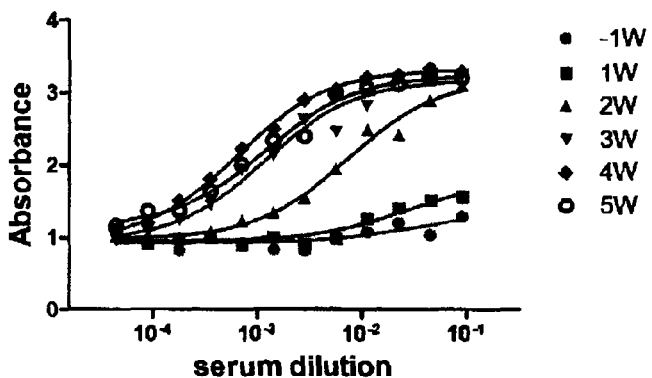
positive control / positive control Fig. 33
(a)
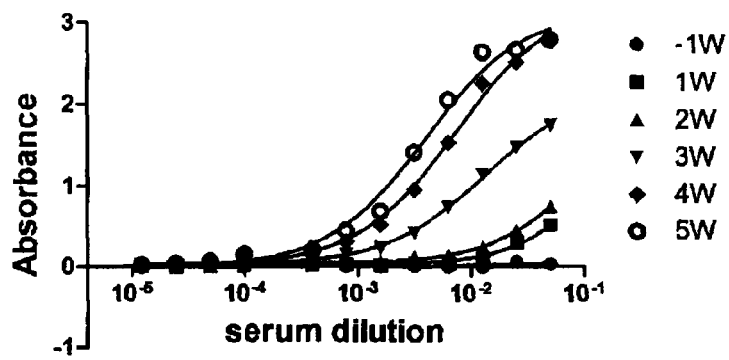
(b)
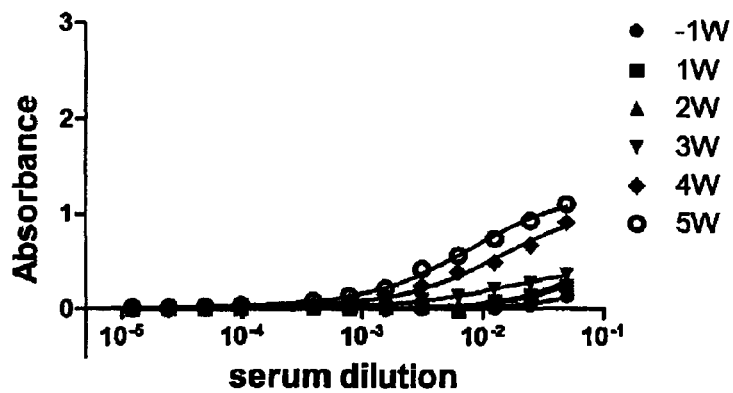

Fig. 34
Anti-HIV activity of serum
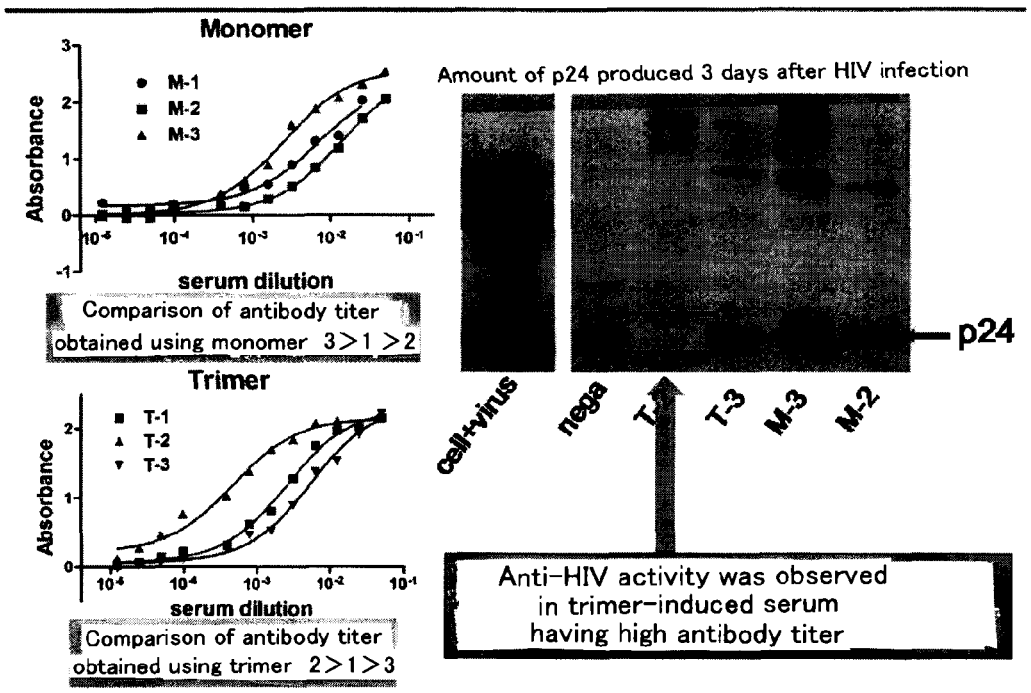
Fig. 35
Evaluation on anti-HIV activity of antigen molecule
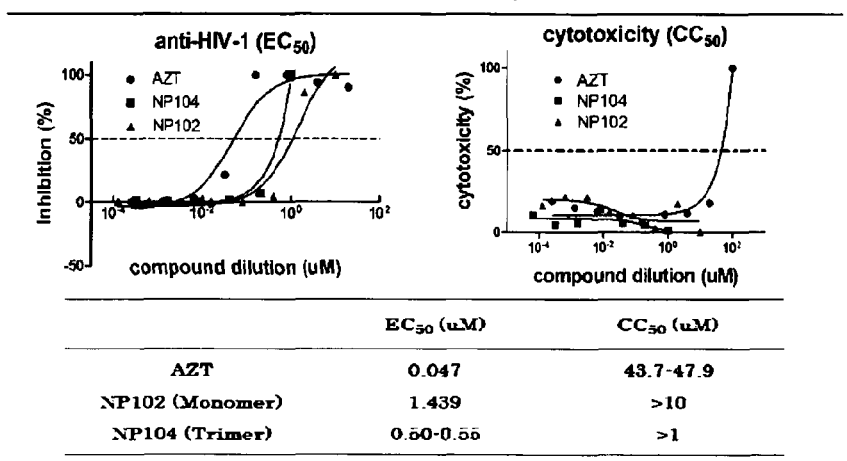
|  | EC$_{50}$ (uM) | CC$_{50}$ (uM) |
| --- | --- | --- |
| AZT | 0.047 | 43.7-47.9 |
| NP102 (Monomer) | 1.439 | >10 |
| NP104 (Trimer) | 0.50-0.55 | >1 |
Monomer and trimer respectively have anti-HIV activity  Native three-dimensional structure is reflected.

PEPTIDIC ANTIGEN THAT INDUCES ANTIBODY RECOGNIZING THREE-DIMENSIONAL STRUCTURE OF HIV AND METHOD FOR SYNTHESIZING SAME

TECHNICAL FIELD

The present invention relates to: a peptide antigen inducing an antibody that recognizes the three-dimensional structure of HIV (human immunodeficiency virus); a method for synthesizing the same; a vaccine comprising the peptide antigen, or an HIV three-dimensional structure-recognizing antibody induced by the peptide antigen; and a preventive and/or therapeutic agent for HIV infection comprising the vaccine or the HIV three-dimensional structure-recognizing antibody as an active ingredient. Particularly, the present invention relates to: a peptide antigen inducing an antibody that recognizes the three-dimensional structure of HIV, wherein in hexamerization of an N-terminal helical region N36 and C34 in an HIV particle transmembrane protein gp41, i.e., the mechanism by which HIV invades a target cell, the peptide antigen inhibits the N36/C34 hexamerization of gp41 by the action of an HIV vaccine on a trimer region of helical region N36 to prevent HIV invasion into a target cell; a method for synthesizing the same; a vaccine comprising the peptide antigen, or an HIV three-dimensional structure-recognizing antibody induced by the peptide antigen; and a preventive and/or therapeutic agent for HIV infection comprising the peptide antigen, the vaccine, or the HIV three-dimensional structure-recognizing antibody as an active ingredient.

BACKGROUND ART

Acquired immunodeficiency syndrome (AIDS) is a disease caused by human immunodeficiency virus (HIV) that was isolated and discovered by Montagnier L. et al., in 1983 (see Non-Patent Document 1). The origin of HIV has been considered to be the ability to infect a human, acquired due to mutation by simian immunodeficiency virus (SIV) whose natural host is a primate. HIV infects hosts not by airborne infection but through 3 main pathways: sexual transmission, blood infection, and mother-to-child transmission. The greatest cause of the sexual transmission is deemed to be contact with sexual discharges. The blood infection is caused by transfusion, wounds, needle-sharing, and so on. Therefore, infection prevention is required from an ethical standpoint. Moreover, the mother-to-child transmission is allegedly caused by contact with body fluids in the birth canal during parturition, maternal breastfeeding, virus movement through the placenta during pregnancy, and so on.

HIV, a species of retrovirus, is an adventitious virus that particularly targets and infects human CD4-positive T cells (see Non-Patent Document 1). HIV that has infected the human CD4-positive T cells is activated after a relatively long incubation period to destroy the T cells. Since T cells play an important role in the immune system, the immune capacity of the body is significantly reduced due to the destroyed T cells. As a result, the body is no longer able to exhibit sufficient resistance even to pathogens that can be eliminated easily in a normal state, falling into a chronic immunodeficient state, i.e., a state called "onset of AIDS".

The number of HIV-infected people has already reached 33 million throughout the world, though the speed at which the number of HIV infections increases is getting slower. In 2007, the number of newly HIV-infected people was 2.4 million, and the number of deaths related to HIV was 2 million (see Non-Patent Document 2). Particularly, in Asia, which has the largest population in the world, HIV infection has rapidly been spreading. Japan is no exception. Although this is an unusual case among developed countries, the number of HIV-infected people is increasing steadily. Specifically, in 2007, the number of AIDS patients was 418, and the number of HIV-infected people was 1082, exceeding 1000 for the first time. Under the present circumstances, such increase remains to be controlled in Japan (see Non-Patent Document 3). However, HIV has been studied actively since its discovery. During years to the present, a method for diagnosing the infectious disease has been established, and overwhelming progress is also seen in therapy, compared with other infectious diseases (see Non-Patent Documents 4 and 5). By virtue of energetic research and development of therapeutic drugs, AIDS is not anymore a disease directly leading to death. However, radical therapy has not been established yet, and new problems have also emerged. Therefore, there is a demand for novel therapeutic drugs.

HIV has proteins called gp120 and gp41 necessary for binding to a target cell, on a viral membrane derived from a host cell. A matrix protein exists as a scaffold protein on the inner surface of the viral membrane and helps maintain the HIV structure. Moreover, the nucleoid of HIV has a regular dodecahedron structure surrounded by capsid proteins and internally contains the RNA genome, integrase (IN), protease (PR), and reverse transcriptase (RT) (FIG. 1). The RNA genome of HIV is approximately 9000 bp long, and the gene cluster is flanked by structures called long terminal repeats (LTRs). A dozen kinds of viral proteins encoded by these genes control complicated replication (see Non-Patent Documents 4 and 5).

A series of multiplication cycles from HIV invasion into a target cell to budding is called life cycle. This life cycle is divided into the following stages (1) to (6): (1) adsorption of the virus onto the cell membrane and membrane fusion; (2) reverse transcription of the RNA genome; (3) viral DNA integration into the host chromosome and replication; (4) processing of the constituent proteins of the virus; (5) construction of virions; and (6) the process of budding. HIV multiplies through these processes (see FIG. 2) (see Non-Patent Documents 4 to 7). Azidothymidine (AZT), the first anti-HIV drug developed in 1985, is a competitive inhibitor of reverse transcriptase. This drug inhibits HIV multiplication by inhibiting the life cycle. Since the development of this AZT, the life cycle of HIV has been revealed in more detail, and the development of anti-HIV drugs has drastically proceeded (see Non-Patent Documents 8 and 9). As a result, anti-HIV drugs as many as 15 or more kinds are currently under clinical application and have enabled highly active anti-retroviral therapy (HAART) in which anti-HIV drugs differing in mechanism of action are used in combination. By virtue of HAART, HIV is not anymore a disease directly leading to death. In addition, the quality of life (QOL) of HIV-infected people has been improved.

The mechanism by which HIV infects a target cell will be described. HIV utilizes a receptor such as CD4 or CXCR4/CXCR5 on the target cell for infecting the target cell. The envelope protein of HIV binds to such a receptor, resulting in change in the three-dimensional structure of the envelop protein, by which the viral membrane of HIV and the target cell membrane are brought close to each other to cause membrane fusion (FIG. 3). When membrane fusion is achieved, the RNA genome or viral proteins of HIV are released into the target cell to achieve infection (see Non-Patent Documents 10 to 15).

Since HIV cannot self-replicate, it can only infect a host cell to use the transcriptional and translational functions of the host cell, for multiplication. Therefore, drugs inhibiting the initial stage of HIV multiplication have received attention. Among such drugs actually under clinical application in the USA and Europe, there is a peptidic drug enfuvirtide (T-20; DP178) (see Non-Patent Documents 16 to 20). This T-20 is a partial peptide of an HIV envelope protein. This partial peptide prevents change in the three-dimensional structure of the HIV envelope protein through its binding to HIV. As a result, the membrane fusion of HIV is inhibited to prevent HIV invasion. Such peptidic HIV multiplication inhibitors are being developed actively, and the development of drugs targeting a co-receptor such as CCR5 or CXCR4 is also proceeding. However, since T-20 is a peptidic inhibitor, its problem is that oral administration is impossible (see Non-Patent Documents 21 to 30).

The RNA genome of HIV that has invaded the target cell is converted to complementary DNA by reverse transcriptase, and this DNA then forms double-stranded DNA (DNA genome) (see FIG. 2). This reverse transcriptase reaction is performed in a complex comprising enzymes and template RNA, and the DNA genome formed by this reverse transcriptase reaction is considered to then translocate into the nucleus. The complex described above is called preintegration complex (PIC). Particularly, viral protein R (vpr) contained in this complex is considered to be responsible for the translocation into the nucleus. After the translocation into the nucleus, the viral DNA genome is inserted into the chromosomal DNA of the host cell by the action of integrase (see Non-Patent Document 31).

Viral RNA, which is the principal body, is synthesized by the transcriptional function of the host cell with the inserted viral genomic DNA as a template. Moreover, viral proteins are also expressed as precursor proteins through transcription, translation, and splicing, and then, these precursor proteins are cleaved into mature proteins by protease. These mature proteins and the HIV RNA genome form a viral core, which is in turn released via the rupture of the cell membrane from within outward to thereby achieve formation of new HIV particles and release thereof from the cell.

The development of inhibitors for the enzymes essential for this life cycle of HIV, such as reverse transcriptase, integrase, and protease, has proceeded, showing a great effect on the inhibition of HIV multiplication. However, the long-term administration of drugs is required for continuously reducing virus loads in the body as much as possible. As a result, there also arise problems such as emergence of drug-resistant strains, a serious adverse reaction, and the need for expensive medical fees for treatment. Particularly, the emergence of drug-resistant viruses is a serious problem. Examples of causes of the emergence of drug-resistant viruses include long-term medication as well as mutability (HIV is highly prone to mutation due to a lack of a DNA repair mechanism such as DNA polymerase).

The base substitution rate of the HIV genome is 1 million or more times that of the mammalian genome; thus, the HIV genome changes at a rate 1 million or more times that of the mammalian genome (see Non-Patent Document 32). As a result, a point mutation is introduced in the nucleotide sequence of the HIV genome, and some strains have acquired resistance to anti-HIV drugs. In addition, cases of cross-resistance have also been reported, in which HIV that has acquired resistance to reverse transcriptase inhibitors, the main drugs in HAART, also acquires resistance to the other reverse transcriptase inhibitors. Thus, there is a demand for the development of drugs with a novel mechanism of action that can be expected to have an effect even on viruses that have acquired drug resistance (see Non-Patent Documents 4, 8, and 33).

Meanwhile, the development of HIV vaccines has been pursued for the purpose of preventing HIV. As a first step, the establishment of HIV animal models was tackled. In the late half of 1980s, the research proceeded drastically by the establishment of SIV-infected macaque monkey models. However, a basic problem, i.e., the extent to which the models reflect human HIV-1 infection, still remains to be solved (see Non-Patent Document 4). This problem holds true not only for vaccine development but for development of new drugs. Specifically, due to concerns about the insufficient reliability of HIV animal models, the possibility cannot be denied that even candidate substances of anti-HIV drugs or anti-HIV vaccine capable of exhibiting an effect on actual human patients infected with HIV are excluded from the screening of substances having an anti-HIV activity using the HIV animal models.

Another problem of the development of vaccines is that the type of immune system that should be induced, i.e., the type of immune system that should be induced for inhibiting the onset of AIDS, is unknown. Although this problem also still remains to be solved, attempts have been made recently to examine the relationship between a number of immune systems such as cell-mediated immunity and humoral immunity and the inhibition of HIV. Currently, there is also a report which concludes that the potentiation of mucosal immunity may also be effective for the inhibition of HIV (see Non-Patent Documents 34 and 35).

Under the circumstances, inactivated virus vaccines were developed as HIV vaccines using monkey models and originally reported to have a protective effect on HIV infection. However, this protective effect on HIV infection was then found to be that on human-derived antigens constituting virions. Thus, the efficacy of the vaccines was denied. Then, attenuated vaccines were shown to have efficacy, but may not be applied clinically at the present moment due to risks attributed to the mutability of HIV as described above. Thus, the development of HIV vaccines has made little progress. However, details on the mechanism by which HIV invades a target cell have been revealed. This has promoted the development of HIV vaccines based on a new point of view.

The mechanism by which HIV invades a target cell will be described. A surface protein gp120 and a transmembrane protein gp41 form a heterodimer on the surface of an HIV particle. The proteins constituting this heterodimer further form homotrimers, and a dozen such homotrimers are present on the HIV cell membrane (FIG. 4). In the course of membrane fusion of HIV, gp120 binds to CD4, a primary receptor for HIV infection, on the target cell to thereby cause its three-dimensional structure change (see Non-Patent Document 9).

Subsequently, gp120, which has become capable of binding to a co-receptor CXCR4 or CCR5, forms a gp120-CD4-co-receptor tripartite complex (see Non-Patent Documents 9 and 10). By the formation of this tripartite complex, gp41 forming the non-covalent complex with gp120 exposes its N terminus, and a membrane-inserted peptide present in gp41 anchors to the target cell membrane. After the anchoring, the N-terminal helical region N36 and C-terminal helical region C34 of gp41 bind to each other in an antiparallel manner to form a hexamer. As a result, the viral membrane of HIV and the target cell membrane are brought close to each other, causing membrane fusion (FIGS. 3 and 5) (see Non-Patent Document 10).

Based on such a mechanism of HIV invasion, some antibodies that target gp120 or gp41 and have an anti-HIV activity have been induced. Currently, b12, 2G12 and the like as antibodies against gp120, and 4E10, 2F5 and the like as antibodies against gp41 are known as those exhibiting a relatively strong anti-HIV activity (FIG. 6) (see Non-Patent Documents 36 to 43). Furthermore, Patent Document 1 describes use of antibodies against gp120 for preventing HIV infection or for inactivating a stage essential for the life cycle of HIV. However, these antibodies, albeit with an anti-HIV activity against a certain HIV strain, did not exhibit a sufficient anti-HIV activity against the other strains, probably because the HIV genome is significantly mutable. Thus, the antibodies still remain to be applied clinically.

PRIOR ART DOCUMENTS

Patent Documents

Patent Document 1: Japanese unexamined Patent Application Publication No. 2009-080118

Non-Patent Documents

Non-Patent Document 1: Sinoussi, B. F., Montagnier, L. Isolation of a T-lymphotropic retrovirus from a patient at risk for acquired immune deficiency syndrome (AIDS). Science 220, 868-871 (1983); Non-Patent Document 2: WHO, World Health Statistics 2008; Non-Patent Document 3: The report of the AIDS Surveillance Committee, the Ministry of Health, Labour and Welfare Japan, "Report on Trend of AIDS Incidence" issued in 2008; Non-Patent Document 4: "Hito Retorovirus Kenkyu no Saizensen (Frontiers of Human Retrovirus Research in English)" ed. by Naoki Yamamoto, issued on Feb. 22, 2002, Springer-Verlag Tokyo, Inc. Non-Patent Document 5: Koyanagi, Y. Outline of the HIV replication and its celluar: the track of an invader in cell. Virus 55, 251-258 (2005); Non-Patent Document 6: Carter, C. A., Ehrlich, L. S. Cell biology of HIV-1 infection of macrophages. Annu. Rev. Macrobiol. 62, 425-443 (2008); Non-Patent Document 7: Eckert, D. M., Kim, P. S. Mechanisms of viral membrane fusion and its inhibition. Annu. Rev. Biochem. 70, 777-810 (2001); Non-Patent Document 8: Baba, M. Recent progress of anti-HIV-1 research. Virus 54, 59-66 (2004); Non-Patent Document 9: Kwong, P. D., Wyatt, R., Robinson, J. Sructure of an HIV gp120 envelope glycoprotein in complex with the CD4 receptor and a neutralizing human antibody. Nature 393, 648-659 (1998); Non-Patent Document 10: Chan, D. C., Fass, D., Kim, P. S. Core structure of gp41 from the HIV envelope glycoprotein. Cell 89, 263-273 (1997); Non-Patent Document 11: Weissenhorn, W., Dessen, A., Harrison, S. C., Skehel, J. J., and Wiley, D. C. Atomic structure of the ectodomain from HIV-1 gp41. Nature 387, 426-430 (1997); Non-Patent Document 12: Tan, K. J., Liu, J., Wang, S., Shen, S., Lu, M. Atomic structure of a thermostable subdomain of HIV-1 gp41. Proc. Natl. Acad. Sci. U.S.A. 94, 12303-12308 (1997); Non-Patent Document 13: Malashkevich, V. N., Chan, D. C., Chutkowski, C. T., Kim, P. S. Crystal structure of the simian immunodeficiency virus (SIV) gp41 core: Conserved helical interactions underlie the broad inhibitory activity of gp41 peptides. Proc. Natl. Acad. Sci. U.S.A. 95, 9134-9139 (1998); Non-Patent Document 14: Lu, M., Blacklow, S. C., Kim, P. S. A trimeric structural domain of the HIV-1 transmembrane glycoprotein. Nat. Struct. Biol. 2(12), 1075-82 (1995); Non-Patent Document 15: Eckert, D. M., Kim, P. S. Design of potent inhibitors of HIV-1 entry from the gp41 N-peptide region. Proc. Natl. Acad. Sci. U.S.A. 98, 11187-11192 (2001); Non-Patent Document 16: Joyce, J. G., Hurni, W. M., Keller, P, M. Enhancement of .alpha.-Helicity in the HIV-1 inhibitory peptide DP178 leads to an increased affinity for human monoclonal antibody 2F5 but does not elicit neutralizing responses in Vitro. J. Biol. Chem. 277, 45811-45820 (2002); Non-Patent Document 17: Kilby, M. J., Eron, J. J. Novel therapies based on mechanisms of HIV-1 cell entry. N. Engl. J. Med. 348, 2228-2238 (2003); Non-Patent Document 18: Kilby, M. J., Hopkins, S., Saag, M. S. Potent suppression of HIV-1 replication in humans by T-20, a peptide inhibitor of gp41-mediated virus entry. Nat. Med. 4, 1302-1307 (1998); Non-Patent Document 19: Lalezari, J. P., Henry, K., O'Hearn, M., Salgo, M. Enfuvirtide, an HIV-1 Fusion Inhibitor, for Drug-Resistant HIV Infection in North and South America. N. Engl. J. Med. 348, 2175-2185 (2003); Non-Patent Document 20: Liu, S., Lu, H., Niu, J., Jiang, S. Different from the HIV fusion inhibitor C34, The anti-HIV drug Fuzeon (T-20) inhibits HIV-1 entry by targeting multiple sites in gp41 and gp120. J. Biol. Chem. 280, 11259-11273 (2005); Non-Patent Document 21: Munch, J., Standker, L., Adermann, K., Schulz, A., Kirchhoff, F. Discovery and optimization of a natural HIV-1 entry inhibitor targeting the gp41 fusion peptide. Cell 129, 263-275 (2007); Non-Patent Document 22: Jiang, S., Lin, K., Lu, M. A conformation-specific monoclonal antibody reacting with fusion-active gp41 from the human immunodeficiency virus type 1 envelope glycoprotein. J. Virol. 72, 10213-10217 (1998); Non-Patent Document 23: Otaka, A., Nakamura, M., Nameki, D., Tamamura, H., Kobayashi, Y., Matsuoka, M., Fujii, N. Remodeling of gp41-C34 peptide leads to highly effective inhibitors of the fusion of HIV-1 with target cells. Angew. Chem. Int. Ed. 16, 2937-2940 (2002); Non-Patent Document 24: Bewley, C. A., Louis, J. M., Ghirlando, R., Clore, G. M. Design of a novel peptide inhibitor of HIV fusion that disrupts the internal trimeric coiled-coil of gp41. J. Biol. Chem. 277, 14238-14245 (2002); Non-Patent Document 25: Welch, B. D., VanDemark, A. P., Heroux, A., Hill, C. P., Kay, M. S. Potent D-peptide inhibitors of HIV-1 entry. Proc. Natl. Acad. Sci. U.S.A. 104, 16828-16833 (2007); Non-Patent Document 26: Louis, J. M., Nesheiwat, I., Chang, L., Clore, G. M., Bewley, C. A. Covalent trimers of the internal N-terminal trimeric coiled-coil of gp41 and antibodies directed against them are potent inhibitors of HIV envelope-mediated cell fusion. J. Biol. Chem. 278, 20278-20285 (2003); Non-Patent Document 27: Bianchi, E., Finotto, M., Ingallinella, P., Renee, H., Pessi, P. Covalent stabilization of coiled coils of the HIV gp41 N region yields extremely potent and broad inhibitors of viral infection. Proc. Natl. Acad. Sci. U.S.A. 102, 12903-12908 (2005); Non-Patent Document 28: Qiao, Z., Kim, M., Reinhold, B., Montefiori, D., Wang, J., Reinherz, E, L. Design, expression, and immunogenicity of a soluble HIV trimeric envelope fragment adopting a prefusion gp41 configuration. J. Biol. Chem. 280, 23138-23146 (2005); Non-Patent Document 29: Eckert, D. M., Malashkevich, V. N., Hong, L. H., Can, P. A., Kim, P. S. Inhibiting HIV-1 entry: discovery of D-peptide inhibitors that target the gp41 coiled-coil pocket. Cell 99, 103-115, (1999); Non-Patent Document 30: Root, M. J., Kay, M. S., Kim, P. S. Protein design of an HIV-1 entry inhibitor. Science 291, 884-888 (2001); Non-Patent Document 31: Masuda, T. Host factors that regulate the intercellular dynamics of HIV-1 genome during the early phase of infection. Virus 1, 41-50 (2006); Non-Patent Document 32:

Sato, H., Yokoyama, M. RNA viruses and mutations. Virus 55, 221-230 (2005); Non-Patent Document 33: Baba M. Advances in antiviral chemotherapy. Virus 55, 69-76 (2005); Non-Patent Document 34: Belyakov, I. M., Berzofsky, J. A. Immunobiology of mucosal HIV infection and the basis for development of a new generation of mucosal AIDS vaccines. Immunity 20, 247-253 (2004); Non-Patent Document 35: Yuki Y, Nochi T, Kiyono H. Progress towards an AIDS mucosal vaccine: An overview. Tuberculosis 87, (2007); Non-Patent Document 36: Alam, M. S., McAdams, M., Boren, D., Haynes, B. F. The role of antibody polyspecificity and lipid reactivity in binding of broadly neutralizing anti-HIV-1 envelope human monoclonal antibodies 2F5 and 4E10 to glycoprotein 41 membrane proximal envelope epitopes. J. Immun. 178, 4424-4435 (2007); Non-Patent Document 37: Cardoso, R. M. F., Zwick, M. B., Stanfield, R. L., Ian A. Wilson, I. A. Broadly Neutralizing Anti-HIV Antibody 4E10 Recognizes a Helical Conformation of a Highly Conserved Fusion-Associated Motif in gp41. Immunity 22, 163-173(2005); Non-Patent Document 38: Ofek, G., Tang, M., Sambor, A., Kwong, P. D. Structure and mechanistic analysis of the anti-human immunodeficiency virus type 1 antibody 2F5 in complex with Its gp41 epitope. J. Virol. 78, 10724-10737 (2004); Non-Patent Document 39: Nelson, J. D., Brunel, F. M., Jensen, R., Michael B. Zwick, M. B. An affinity-enhanced neutralizing antibody against the membrane-proximal external region of human immunodeficiency virus type 1 gp41 recognizes an epitope between those of 2F5 and 4E10. J. Virol. 81, 4033-4043 (2007); Non-Patent Document 40: Conley, A. J., Kessler, I. I., Boots, J. L., Tung, S. J., Arnold, B. A., Keller, P. M., Shaw, A. R., Emini, E. A. Neutralization of divergent human immunodeficiency virus type 1 variants and primary isolates by IAM-41-2F5, an anti-gp41 human monoclonal antibody. Proc. Natl. Acad. Sci. U.S.A. 91, 3348-3352 (1994); Non-Patent Document 41: Trkola, A., Purtscher, T. M., Muster, C. Ballaun, A. Buchacher, N. Sullivan, K. Srinivasan, J. Sodroski, Moore, J. P., Katinger, H. Human monoclonal antibody 2G12 defines a distinctive neutralization epitope on the gp120 glycoprotein of human immunodeficiency virus type 1. J. Virol. 70, 1100-1108 (1996); Non-Patent Document 42: Hewer, R., Meyer, D. Peptide Immunogens based on the envelope region of HIV-1 are recognized by HIV/AIDS patient polyclonal antibodies and induce strong humoral immune responses in mice and rabbits. Mol. Immune. 40, 327-335 (2003); and Non-Patent Document 43: Pantophlet, R., Saphire, E. O., Poignard, P., Burton, P. D. Fine mapping of the interaction of neutralizing and normeutralizing monoclonal antibodies with the CD4 binding site of human immunodeficiency virus type 1 gp120. J. Virol. 77, 642-658 (2003).

SUMMARY OF THE INVENTION

Object to be Solved by the Invention

A problem of the development of HIV vaccines is that previous approaches effective for infectious diseases, such as attenuated vaccines and live vaccines, are regarded as dangerous due to the mutability of HIV and therefore, can no longer be used. Moreover, antibody induction is usually performed for the purpose of synthesizing a partial sequence of the protein of HIV and inducing antibodies sequence-specific for the partial sequence. However, a problem of the antibodies induced using such a partial sequence is generally low specificity or binding activity for the three-dimensional structure of a neutralization target, though these antibodies are capable of specifically binding to the amino acid sequence.

Thus, an object of the present invention is to provide an HIV antibody-inducing peptide antigen that can be used without problems for such HIV, which is highly prone to mutation, and is effective in developing an antibody or a vaccine having excellent specificity and binding activity even for the three-dimensional structure of a neutralization target, i.e. the mechanism by which HIV invades a target cell; a method for synthesizing the same; a vaccine comprising the peptide antigen, or an HIV three-dimensional structure-recognizing antibody induced by the peptide antigen; and a preventive and/or therapeutic agent for HIV infection comprising the vaccine or the HIV three-dimensional structure-recognizing antibody as an active ingredient.

Means to Solve the Object

The present inventor has conducted diligent studies to attain the object and consequently had the idea that for targeting HIV highly prone to mutation, it is desirable to induce antibodies that recognize and bind to not only the amino acid sequence but also the three-dimensional structure. Thus, the present inventor has assumed that an antibody having a higher neutralizing activity even against HIV can be induced if antibodies specific also for the three-dimensional structure can be induced by using an antigen molecule that preserves the three-dimensional structure. Thus, for the purpose of targeting gp41, a key to membrane fusion in the mechanism by which HIV invades a target cell, and developing an antigen molecule for inducing antibodies that specifically recognize an intermediate structure thereof, a trimer of a portion called N36 most important in the helical region of gp41 was chemically synthesized as an antigen molecule. As a result, it has been found that use of this antibody-inducing antigen molecule can provide an HIV antibody-inducing peptide antigen that is effective in developing an antibody or a vaccine having excellent specificity and binding activity even for the three-dimensional structure of a neutralization target, i.e., the mechanism by which HIV invades a target cell. Based on these findings, the present invention has been completed.

Specifically, the present invention provides a method for synthesizing a peptide antigen inducing an HIV three-dimensional structure-recognizing antibody that recognizes a trimer region of N36, the method comprising the steps of: synthesizing, as an antigenic peptide, a derivative of a helical region N36 peptide at N-terminal of an HIV particle transmembrane protein gp41; and synthesizing a trimer of the N36 peptide derivative by ligating the N36 peptide derivative to a C3-symmetric template compound having three equivalent linker structures.

The present invention will be summarized. As a result of conducting studies to develop HIV vaccines as therapy for AIDS and HIV infection patients, the present inventor has paid attention to membrane fusion that occurs at the initial stage of infection, and aimed for developing HIV vaccines toward the treatment of HIV infection. In the mechanism underlying the membrane fusion, the HIV surface protein constituting the trimeric structure is spiked to a host cell membrane, and then, the C-terminal helical region C34 of gp41 binds in an antiparallel manner to the N-terminal helical region N36 of gp41 to form a hexamer (6-helical bundle) structure. As a result, the membranes of the host cell and HIV are brought close to each other, causing membrane fusion to achieve infection (FIG. 3). Thus, the present inventor has assumed that if an antibody that specifically recognizes the trimeric structure of gp41 at a stage prior to the hexameric structure can be induced, HIV invasion can be inhibited by inhibiting the formation of the hexameric structure. Therefore, the trimeric structure of N36 was developed as an antigen molecule by chemical synthesis.

First, N36-derived peptides of interest were synthesized by an Fmoc (9-fluorenylmethoxycarbonyl)-solid-phase synthesis method. Subsequently, a low-molecular-weight template compound having three equivalent linkers, which would facilitate the formation of a trimeric structure, was designed and synthesized. Furthermore, a thiazolidine ligation method has previously been reported, which utilizes the binding of the N-terminal Cys of a peptide to glycolaldehyde ester via the formation of thiazolidine. A trimer-mimicking antigen molecule was successfully synthesized by accumulating the peptides onto the template compound using the method.

In the present invention, the N36 peptide derivative in the step of synthesizing, as an antigenic peptide, a derivative of a helical region N36 peptide at N-terminal of an HIV particle transmembrane protein gp41 can be synthesized by a solid-phase synthesis method using selective deprotection of a 9-fluorenylmethoxycarbonyl (Fmoc) group and a condensation reaction.

Furthermore, in the step of synthesizing, as an antigenic peptide, a derivative of a helical region N36 peptide at N-terminal of an HIV particle transmembrane protein gp41, Cys necessary for the ligation to the template compound is introduced to the N36 peptide derivative, and one residue of Gly is introduced as a spacer between the sequence of native N36 and the Cys to prevent reduction in reactivity caused by steric hindrance. This procedure can improve the ligation to the template compound and further prevent reduction in reactivity caused by steric hindrance between the native sequence and Cys.

In the present invention, a compound represented by the following general formula (1) or a salt thereof can be used as the C3-symmetric template compound having three equivalent linker structures in the step of synthesizing a trimer of the N36 peptide derivative by ligating the N36 peptide derivative to a C3-symmetric template compound having three equivalent linker structures:

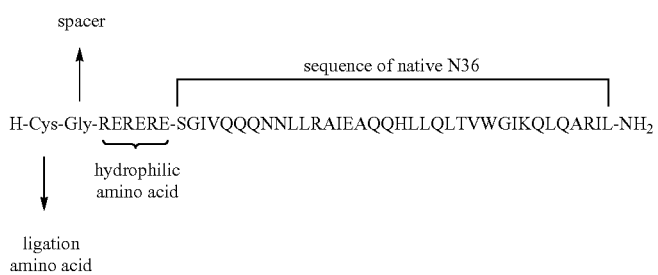

(1)

wherein X represents a positive integer.

A template compound of the above-described general formula wherein X is an integer within the range of 1 to 5 is selected as a preferable compound. Particularly, a compound represented by the following general formula (2) or a salt thereof can be selected as a preferable template compound:

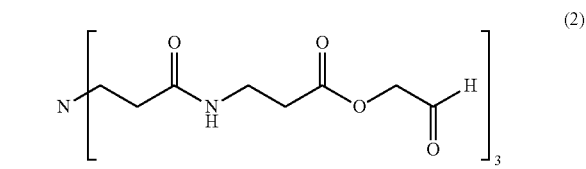

(2)

In the present invention, the N36 peptide derivative in the step of synthesizing, as an antigenic peptide, a derivative of a helical region N36 peptide at N-terminal of an HIV particle transmembrane protein gp41 can be obtained by adding a total of 6 residues of hydrophilic amino acids Arg and Glu to N terminus of the N36 peptide to enhance water solubility, further placing Cys (which is used in thiazolidine ligation) to N terminus thereof, and placing Gly as a spacer between the Cys and Arg residues to prevent reduction in reactivity caused by steric hindrance. Examples of such an N36 peptide derivative can include compounds represented by the following general formula (3):

(3)

spacer
↓
                  sequence of native N36

H-Cys-Gly-RERERE-SGIVQQQNNLLRAIEAQQHLLQLTVWGIKQLQARIL-NH₂
        ↓
    hydrophilic
    amino acid ligation
amino acid In the present invention, the trimer of the N36 peptide derivative can be synthesized by stirring the C3-symmetric template compound having three equivalent linker structures and the N36 peptide derivative with an acetate buffer thus synthesized in the present invention to thereby ligate the N36 peptide derivative described above to the C3-symmetric template compound having three equivalent linker structures.

In the present invention, a template compound represented by a compound represented by the above-described general formula (1) (wherein X represents a positive integer) or a salt thereof can be used. Particularly, a template compound of the general formula wherein X is an integer within the range of 1 to 5 can be used preferably.

In the present invention, a host animal can be sensitized with a peptide antigen inducing an HIV three-dimensional structure-recognizing antibody, which is synthesized by the peptide antigen synthesis method of the present invention, to induce an antibody against the antigen. Moreover, an HIV vaccine can be produced using the peptide antigen inducing an HIV three-dimensional structure-recognizing antibody. The present invention can provide a preventive and/or therapeutic agent for HIV infection comprising, as an active, ingredient, the HIV three-dimensional structure-recognizing antibody that recognizes a trimer region of N36, or the HIV vaccine. The preventive and/or therapeutic agent for HIV infection of the present invention can exert preventive and/or therapeutic effects on HIV infection in the prevention and/or treatment of HIV infection by inhibiting N36/C34 hexamerization of gp41 by the action of the HIV three-dimensional structure-recognizing antibody or the HIV vaccine on a trimer region of a helical region N36 at N-terminal of the HIV particle transmembrane protein gp41 to prevent HIV invasion into a target cell.

Effect of the Invention

The present invention can provide an HIV antibody-inducing peptide antigen that is effective in developing an antibody or a vaccine having excellent specificity and binding activity even for the three-dimensional structure of a neutralization target, i.e., the mechanism by which HIV invades a target cell. The HIV antibody-inducing peptide antigen provided by the present invention enables production of an HIV three-dimensional structure-recognizing antibody or a vaccine and can provide a preventive and/or therapeutic agent for HIV infection comprising the peptide antigen, the vaccine, or the HIV three-dimensional structure-recognizing antibody as an active ingredient. A problem of the development of HIV vaccines is that previous approaches effective for infectious diseases, such as attenuated vaccines and live vaccines, are regarded as dangerous due to the mutability of HIV and therefore, can no longer be used. However, the HIV antibody-inducing peptide antigen of the present invention can provide an HIV antibody-inducing peptide antigen that is effective in developing an antibody or a vaccine having specificity and a binding activity not only for the targeted amino acid sequence of HIV, which is highly prone to mutation, but for the three-dimensional structure of a neutralization target, i.e., the mechanism by which HIV invades a target cell. Thus, the above-described problem of the conventional development of HIV vaccines can be solved, and an HIV antibody or an HIV vaccine that is safe and effective for HIV infection can be provided. As a result, a preventive and/or therapeutic agent for HIV infection that is safe and effective for HIV infection can be provided.

BRIEF DESCRIPTION OF DRAWINGS

FIG. 7 is a diagram showing a scheme to synthesize an MAP-N36 peptide antigen molecule.
FIG. 8 is a diagram showing a scheme to synthesize an antigenic peptide by an Fmoc solid-phase synthesis method.
FIG. 9(a) is a diagram showing the amino acid sequence of NP101, etc.;
FIG. 9(b) is a diagram showing an HPLC chart after purification of NP101;
and FIG. 9(c) is a diagram showing results of MALDI-TOF MS after HPLC.
FIG. 10(a) is a diagram showing the amino acid sequence of the positive control antigen, etc.;
FIG. 10(b) is a diagram showing an HPLC chart after purification of the positive control antigen;
FIG. 10(c) is a diagram showing divalent ion peaks in ESI-TOF MS after HPLC;
and FIG. 10(d) is a diagram showing ion peaks reconstituted from polyvalent forms.
FIG. 11 is a diagram related to the synthesis of MAP.
FIG. 11(a) is a diagram showing the amino acid sequence of MAP, etc.;
FIG. 11(b) is a diagram showing an HPLC chart after purification of MAP;
and FIG. 11(c) is a diagram showing the $[M+H]^+$ and $[M+2H]^{2+}/2$ ion peaks of MAP in ESI-TOF MS after HPLC.
FIG. 17 is a diagram showing results of evaluating antibody titers in serum by ELISA.
FIG. 17(a) is a diagram showing results of ELISA using an "NP101-MAP-immobilized plate" and "serum obtained by the administration of a negative control";
FIG. 17(b) is a diagram showing results of ELISA using an "NP101-MAP-immobilized plate" and "serum obtained by the administration of NP101-MAP";
and FIG. 17(c) is a diagram showing results of ELISA using an "positive control-MAP-immobilized plate" and "serum obtained by the administration of positive control-MAP".
FIG. 19(a) is a diagram showing the amino acid sequence of NP102, etc.;
FIG. 19(b) is a diagram showing an HPLC chart after purification of NP102;
FIG. 19(c) is a diagram showing the $[M+4H]^{4+}/4$ ion peaks of NP102 in ESI-TOF MS after HPLC;
and FIG. 19(d) is a diagram showing ion peaks reconstituted from polyvalent forms.
FIG. 20(a) is a diagram showing the amino acid sequence of NP103, etc.;
FIG. 20(b) is a diagram showing an HPLC chart after purification of NP103;
FIG. 20(c) is a diagram showing the $[M+2H]^{2+}/2$ to $[M+5H]^{5+}/5$ ion peaks of NP103 in ESI-TOF MS after HPLC;
and FIG. 20(d) is a diagram showing ion peaks reconstituted from polyvalent forms.
FIG. 26(a) is a diagram showing a schematic view of NP104, etc.;
FIG. 26(b) is a diagram showing an HPLC chart after purification of NP104;
FIG. 26(c) is a diagram showing the $[M+6H]^{6+}/6$ to $[M+15H]^{15+}/15$ ion peaks of NP103 in ESI-TOF MS after HPLC;
and FIG. 26(d) is a diagram showing ion peaks reconstituted from polyvalent forms.

FIG. 27 is a diagram showing a retention time in HPLC and ESI-TOF-MS identification results during the synthesis of NP104.

FIG. 28 is a diagram showing CD spectra for NP102 and NP104.

FIG. 29 is a diagram showing the molar ellipticities and α-helix contents of NP102 and NP104.

FIG. 30 is a diagram showing the schedule of immunization and collection of blood in an antibody induction experiment using NP104, etc.

FIG. 31 is a diagram showing results of evaluating antibody titers in serum by ELISA. FIG. 31(a) is a diagram showing results of ELISA using an "NP102-immobilized plate" and "serum obtained by the administration of a negative control"; and FIG. 31(b) is a diagram showing results of ELISA using an "NP104-immobilized plate" and "serum obtained by the administration of a negative control".

FIG. 32 is a diagram showing results of evaluating antibody titers in serum by ELISA. FIG. 32(a) is a diagram showing results of ELISA using an "NP102-immobilized plate" and "serum obtained by the administration of NP102"; FIG. 32(b) is a diagram showing results of ELISA using an "NP104-immobilized plate" and "serum obtained by the administration of NP104"; and FIG. 32(c) is a diagram showing results of ELISA using a "positive control-immobilized plate" and "serum obtained by the administration of the positive control".

FIG. 33 is a diagram showing results of evaluating antibody titers in serum by ELISA. FIG. 33(a) is a diagram showing results of ELISA using an "NP104-immobilized plate" and "serum obtained by the administration of NP102"; and FIG. 33(b) is a diagram showing results of ELISA using an "NP102-immobilized plate" and "serum obtained by the administration of NP104".

FIG. 34 is a diagram showing results of evaluating the HIV infection inhibitory effect of serum containing an antibody of the present invention. The upper left panel is a diagram showing results of ELISA using an "NP102-immobilized plate" and "serum obtained by the administration of NP102"; the lower left panel is a diagram showing results of ELISA using an "NP104-immobilized plate" and "serum obtained by the administration of NP104"; and the right panel is a diagram showing results of p24 assay.

FIG. 35 is a diagram showing results of evaluating the anti-HIV activity of serum containing the antibody of the present invention by MTT assay. The upper left panel is a diagram showing the anti-HIV activity ($EC_{50}$ (μM)); the upper right panel is a diagram showing cytotoxicity ($CC_{50}$ (μM)); and the lower panel is a diagram summarizing $EC_{50}$ (μM) and $CC_{50}$ (μM).

MODE OF CARRYING OUT THE INVENTION

Figure 1:
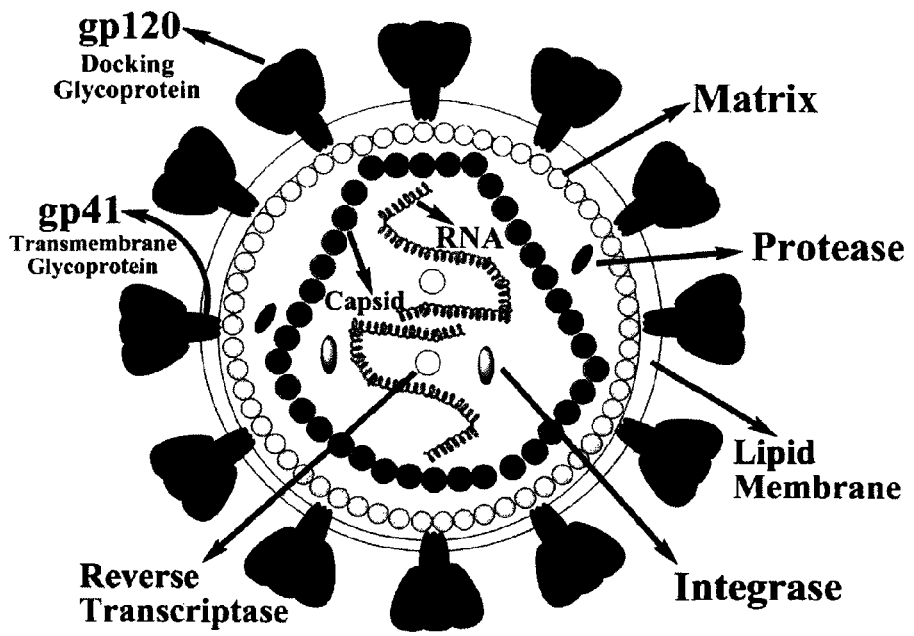
FIG. 1 is a diagram showing a schematic view of HIV.
Figure 2:
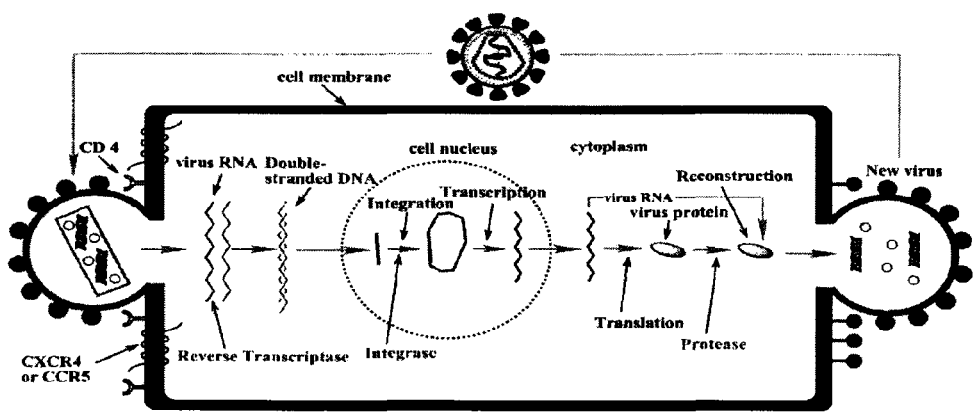
FIG. 2 is a diagram showing the life cycle of HIV.
Figure 3:
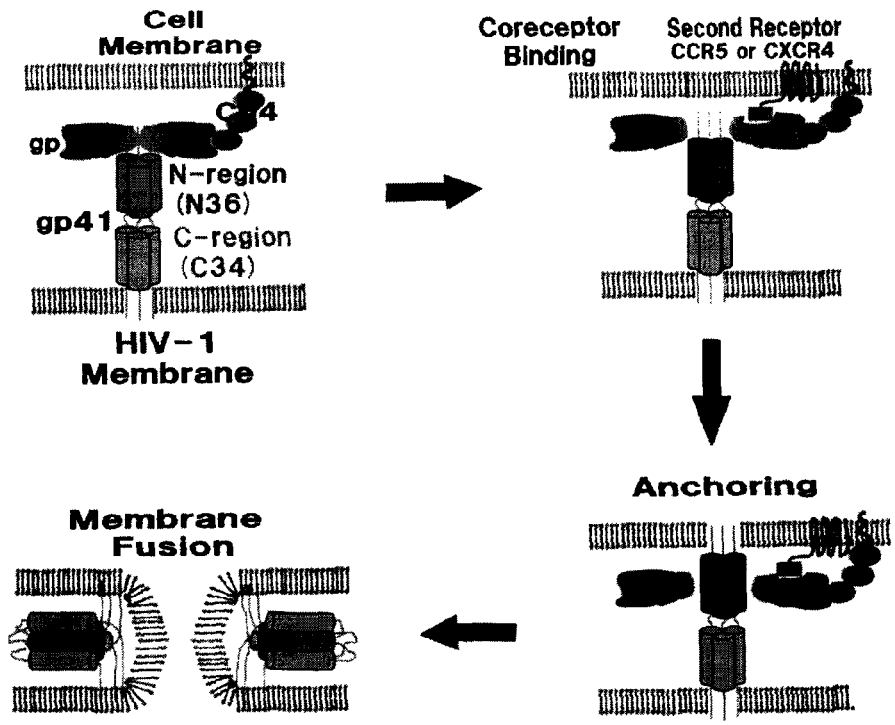
FIG. 3 is a diagram showing the membrane fusion mechanism of HIV.
Figure 4:
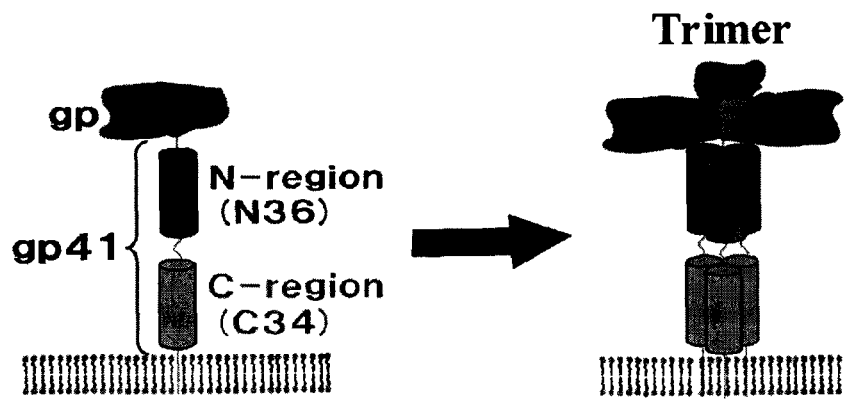
FIG. 4 is a diagram showing the trimeric structure of an HIV envelope protein gp41.
Figure 5:
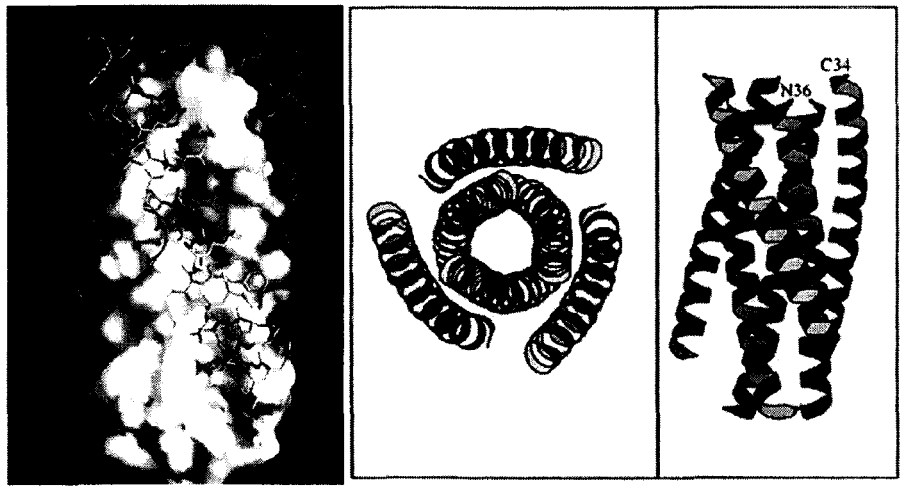
FIG. 5 is a diagram showing results of X-ray crystal structure analysis on the hexameric structure of gp41 in membrane fusion.
Figure 6:
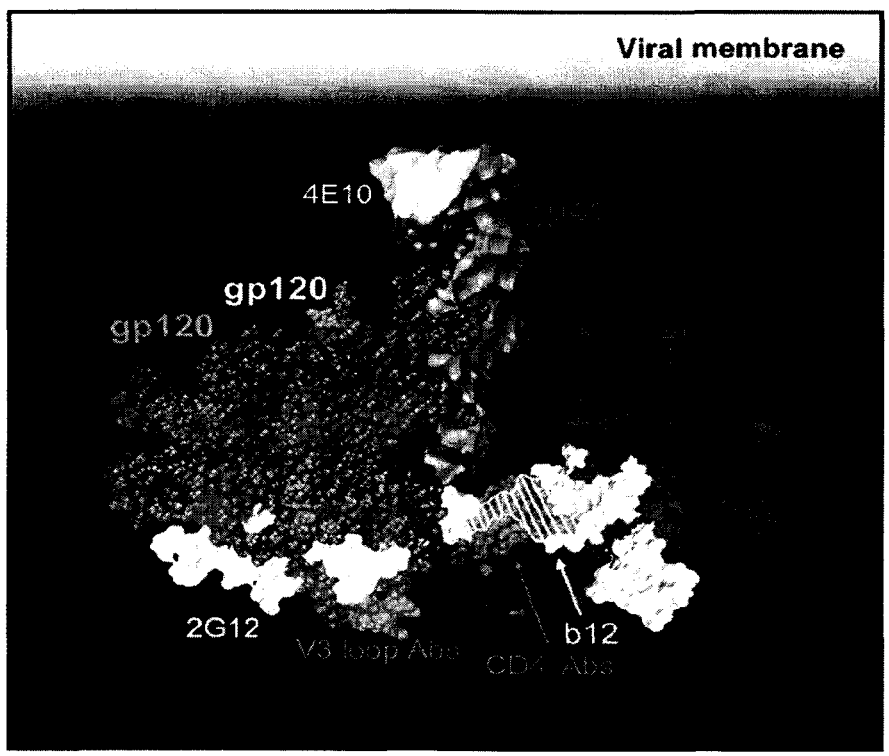
FIG. 6 is a diagram showing the name of an antibody against an HIV envelope protein and its recognition region.

The present invention provides a method for synthesizing a peptide antigen inducing an HIV three-dimensional structure-recognizing antibody that recognizes a trimer region of N36 (hereinafter, also simply referred to as a "peptide antigen synthesis method of the present invention"), the method comprising the steps of: synthesizing a derivative of a helical region N36 peptide at N-terminal of an HIV particle transmembrane protein gp41 (hereinafter, also simply referred to as an "N36 peptide derivative"); and synthesizing a trimer of the N36 peptide derivative by ligating the N36 peptide derivative to a C3-symmetric template compound having three equivalent linker structures (hereinafter, also simply referred to as a "template compound according to the present invention").

The N36 peptide derivative according to the present invention means peptides that consist of an amino acid sequence derived from the amino acid sequence (SEQ ID NO: 1) of the N36 peptide by the substitution, deletion, or insertion of one or two or more (preferably 2 to 15, more preferably 2 to 10, even more preferably 2 to 5) amino acids and can be used in the synthesis of the peptide antigen inducing an HIV three-dimensional structure-recognizing antibody. Preferable examples of such an N36 peptide derivative can include peptides obtained by placing Cys (which is used in thiazolidine ligation) at N terminus of the N36 peptide. More preferable examples thereof can include peptides obtained by adding a total of 6 residues of hydrophilic amino acids Arg and Glu to N terminus of the N36 peptide to enhance water solubility, further placing Cys (which is used in thiazolidine ligation) at N terminus thereof, and placing Gly as a spacer between the Cys and Arg to prevent reduction in reactivity caused by steric hindrance. Particularly preferable examples thereof can include compounds represented by the above-described general formula (3). In this context, whether a certain N36 peptide derivative is peptide that can be used in the synthesis of the peptide antigen inducing an HIV three-dimensional structure-recognizing antibody can be confirmed by examining whether the peptides are capable of inducing an HIV three-dimensional structure-recognizing antibody that recognizes a trimer region of N36.

In the step of synthesizing an N36 peptide derivative in the peptide antigen synthesis method of the present invention, the N36 peptide derivative can be synthesized using Fmoc solid-phase peptide synthesis (SPPS) (see Hirokazu Tamamura et al., Bioorganic & Medicinal Chemistry 6 (1998), 1033-1041; and "Solid phase peptide synthesis—a practical approach" by E Atherton & R C Sheppard IPI PRESS). Specifically, the peptides of interest can be synthesized by the solid-phase synthesis method by repeating the procedures of selective deprotection of a protective group 9-fluorenylmethoxycarbonyl (Fmoc) group for the amino group of the principal chain and condensation reaction, finally followed by cleavage from resin and deprotection.

In the present invention, the template compound of the present invention is used in the step of synthesizing a trimer of the N36 peptide derivative. Preferable examples of the template compound of the present invention can include a compound represented by the following general formula (1) or a salt thereof:

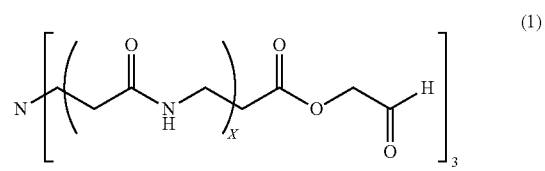

wherein X represents a positive integer.

The moiety X is preferably an integer within the range of 1 to 5, more preferably an integer within the range of 1 to 3, particularly preferably 1, from the viewpoint of obtaining a trimer of the N36 peptide derivative more analogous to the trimeric structure of N36 in the native gp41 protein. By use of such a template compound, the N36 peptide derivative can be trimerized conveniently into a structure analogous to the native structure. The glycolaldehyde ester moiety at the end of the template compound of the present invention can be used in thiazolidine ligation with a carrier protein-coupled N36 peptide derivative. Moreover, the amide bond has the advantage that it enhances hydrophilicity and permits easy synthesis.

Figure 22:
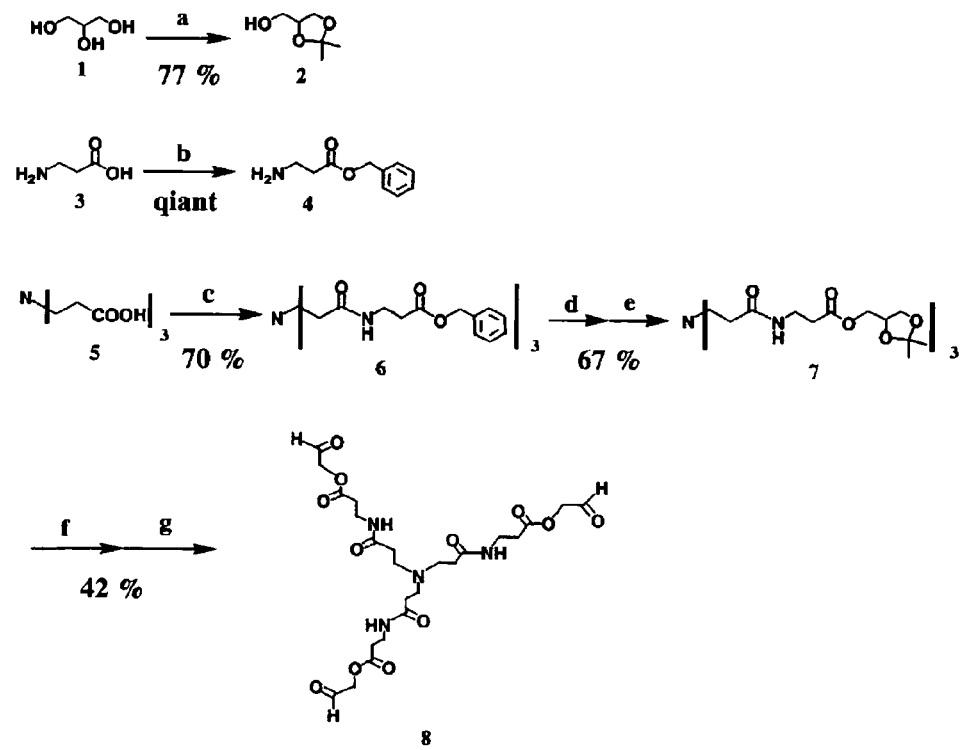
FIG. 22 is a diagram showing a scheme to synthesize the template compound.

The template compound of the present invention may be in the form of a salt such as an acid-addition salt or a base-addition salt. Examples of the acid-addition salt can include: mineral acid salts such as hydrochloride, phosphate, nitrate, sulfate, acetate, propionate, butyrate, valerate, citrate, fumarate, maleate, and malate; and organic acid salts such as oxalate or tartrate. Moreover, examples of the base-addition salt can include: metal salts such as sodium salt, potassium salt, magnesium salt, or calcium salt; ammonium salt; or organic amine salts such as triethylamine salt or ethanolamine salt. Furthermore, the template compound of the present invention may have one or two or more arbitrary substituents as long as it can be used in the present invention. When the template compound of the present invention has two or more substituents, they may be the same or different. The position at which each substituent is present is not limited as long as it can be used in the present invention. The substituents can be present at arbitrary replaceable sites. The types of the substituents are not particularly limited. The template compound of the present invention can be prepared by, for example, a method summarized in FIG. 22 described later and can specifically be prepared by a method described in the paragraph (3) of Example 1 described later.

In the step of synthesizing a trimer of the N36 peptide derivative by ligating the N36 peptide derivative according to the present invention to the template compound of the present invention, a thiazolidine ligation reaction can be used for forming the trimer of the N36 peptide derivative (Biologicals, 29, 189-196, 2001; Biopolymers, 60, 194-205, 2001; Proc. Natl. Acad. Sci. U.S.A., 91, 6584-6588, 1994; J. Am. Chem. Soc. 123, 2487-3494, 2001: 125, 73-82, 2002: 121, 9013-9022, 1999; and Biopolymers, 90, 320-329, 2008).

Specifically, the thiazolidine ligation reaction is a method by which unprotected peptide fragments are ligated to each other via a pseudoproline structure. In this reaction, the amino group of N-terminal Cys in one peptide initiates the nucleophilic attack on a carbonyl carbon atom in the other peptide having a C-terminal peptidyl glycolaldehyde ester to form imine. Subsequently, thiazolidine ring formation takes place by the molecular nucleophilic attack by the thiol group in the side chain of cysteine within the molecule. Through this reaction, thiazolidine ester is formed, and then, an O,N-acyl migration reaction can occur to thereby form a stable pseudoproline bond.

Many methods for ligation based on this pseudoproline bond have been developed so far. It is known that not only Cys but also Trp, Ser, Thr, His, or Asn assumes a similar structure for ligation. Among them, Cys has been reported to produce particularly high reactivity and high yields (J. Am. Chem. Soc. 121, 9013-9022, 1999). This reaction occurs in a buffer adjusted to pH 4 to 6, i.e., under mild conditions, and proceeds even in a buffer reduced by mixing with tris(2-carboxyethyl)phosphine hydrochloride (TCEP). Thus, the formation of inconvenient bonds such as disulfide bonds between Cys residues can be prevented.

Preferable examples of a method for the thiazolidine ligation reaction can include methods comprising synthesizing a trimer of the N36 peptide derivative by stirring an acetate buffer, more preferably 200 mM acetate buffer (pH=5.2) and 20% 2,2,2-trifluoroethanol (TFE), containing the linker compound of the present invention and the N36 peptide derivative thus synthesized in the present invention to thereby ligate the N36 peptide derivative to the C3-symmetric template compound having three equivalent linker structures. Such a thiazolidine ligation reaction occurs specifically for the N-terminal Cys of the N36 peptide derivative. The course of the reaction can be monitored using HPLC and ESI-TOF-MS to detect the completion of the reaction.

The peptide antigen inducing an HIV three-dimensional structure-recognizing antibody according to the present invention (hereinafter, also simply referred to as a "peptide antigen of the present invention") is not particularly limited as long as it is a peptide antigen synthesized by the peptide antigen synthesis method of the present invention. Preferable examples thereof can include a peptide antigen (trimer of the N36 peptide derivative) represented by the following general formula (4) (wherein X represents a positive integer; and Monomer represents an N36 peptide derivative):

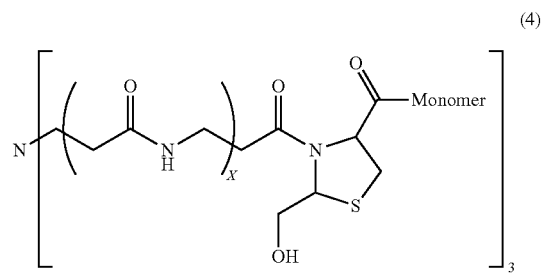

(4)

X in the above-described general formula (4) is preferably an integer within the range of 1 to 5, more preferably an integer within the range of 1 to 3, particularly preferably 1, from the viewpoint of obtaining a trimer of the N36 peptide derivative more analogous to the trimeric structure of N36 in the native gp41 protein.

In the present invention, a host animal can be sensitized with the peptide antigen of the present invention to induce an antibody against the antigen (hereinafter, also simply referred to as an "antibody according to the present invention") according to a routine method. This antibody according to the present invention is an HIV three-dimensional structure-recognizing antibody that recognizes a trimer region of N36. The antibody according to the present invention includes a human antibody. In this context, the "human antibody" according to the present invention means an antibody which is an expression product of a human-derived antibody gene. The human antibody can be obtained by administering the peptide antigen of the present invention to transgenic animals that contain an introduced human antibody gene locus and are capable of producing human-derived antibodies. Examples of the transgenic animals include mice. Examples of mice capable of producing human antibodies can include mice that are deficient in endogenous mouse immunoglobulin (Ig) heavy and κ-light chains and preserve a human Ig heavy chain gene-containing chromosome 14 fragment (SC20) and a human Ig κ chain transgene (KCo5) at the same time. These mice are prepared by the crossing between mice of lineage A having the human Ig heavy chain gene locus and mice of lineage B having the human Ig κ chain transgene. The lineage A is a mouse lineage that is homozygous for both the disruptions of endogenous Ig heavy and κ-light chains and preserves the chromosome 14 fragment (SC20) that can be transmitted to progeny (Tomizuka. et al., Proc Natl Acad Sci USA., 2000, Vol. 97: 722). Moreover, the lineage B is a mouse lineage that is homozygous for both the deficiencies of endogenbus mouse Ig heavy and κ-light chains and preserves the human Ig κ chain transgene (KCo5) (Nat Biotechnol., 1996 Vol. 14: 845).

Moreover, any of polyclonal and monoclonal antibodies and functional fragments thereof is incorporated in the antibody according to the present invention as long as it is an HIV three-dimensional structure-recognizing antibody that recognizes a trimer region of N36. The functional fragment of the antibody according to the present invention means a fragment of an antibody specifically binding to an antigen to which the antibody according to the present invention specifically binds. More specifically, examples thereof include F(ab')$_2$, Fab', Fab, Fv, disulphide-linked FV, single-chain FV (scFv), and polymers thereof (D. J. King, Applications and Engineering of Monoclonal Antibodies, 1998, T. J. International Ltd). Such a functional fragment can be obtained by a routine method, for example, protease (e.g., papain or pepsin) digestion of antibody molecules, or by a genetic engineering approach known in the art.

The polyclonal antibody according to the present invention can be produced, for example, by a method described below. The polyclonal antibody is obtained by immunizing non-human mammals such as mice, rabbits, goats, or horses with the peptide antigen of the present invention, together with an immunostimulant (Freund's adjuvant, etc.), if necessary. The monoclonal antibody according to the present invention can be obtained by preparing hybridomas from antibody-producing cells obtained from immunized animals and myeloma cells having no ability to produce autoantibodies, cloning the hybridomas, and selecting clones producing monoclonal antibodies that exhibit specific affinity for the antigen used in the immunization. The hybridoma preparation can be performed according to the method of Kohler and Milstein, et al. (Nature, 1975, Vol. 256: 495-497) or a method equivalent thereto. The monoclonal antibody-producing hybridoma clones can be screened by culturing the hybridomas in, for example, microtiter plates, and assaying the reactivity of a culture supernatant in wells in which proliferation has been observed, with the immunizing antigen using an immunological method such as enzyme immunoassay (e.g., ELISA), radioimmunoassay, or a fluorescent antibody method.

To produce monoclonal antibodies from the hybridomas, the hybridomas are cultured in vitro, and the monoclonal antibodies can be isolated from the culture supernatant. Alternatively, the hybridomas are cultured in vivo, for example, in the ascitic fluids of mice, rats, guinea pigs, hamsters, rabbits, or the like, and the monoclonal antibodies can also be isolated from the ascitic fluids. Also, a monoclonal antibody-encoding gene is cloned from antibody-producing cells such as hybridomas and incorporated in appropriate vectors, with which hosts (e.g., mammalian cell lines such as Chinese hamster ovary (CHO) cells, *E. coli*, yeast cells, insect cells, and plant cells) are then transformed. Recombinant antibodies can be prepared from the hosts using a gene recombination technique (P. J. Delves, ANTIBODY PRODUCTION ESSENTIAL TECHNIQUES, 1997 WILEY, P. Shepherd and C. Dean, Monoclonal Antibodies, 2000 OXFORD UNIVERSITY PRESS, J. W. Goding, Monoclonal Antibodies: principles and practice, 1993 ACADEMIC PRESS).

Furthermore, transgenic cow, goats, sheep, or pigs containing the antibody gene of interest incorporated in the endogenous gene are prepared using a transgenic animal preparation technique, and antibodies derived from the antibody gene may be obtained at a large scale from the milk of the transgenic animals.

The produced antibodies can be purified by appropriate combination of methods well known in the art, for example, chromatography using protein A columns, ion-exchange chromatography, hydrophobic chromatography, ammonium sulfate precipitation, gel filtration, and affinity chromatography.

Moreover, an HIV vaccine can be produced using the peptide antigen of the present invention. The peptide antigen or the HIV vaccine can also be administered to a subject to thereby induce the antibody according to the present invention in the subject. The present invention can provide a preventive and/or therapeutic agent for HIV infection comprising the peptide antigen, the antibody, or the HIV vaccine of the present invention as an active ingredient. The antibody or the HIV vaccine can be produced using a method usually used in HIV antibody or HIV vaccine production, in addition to using the peptide antigen of the present invention.

Dosage forms usually adopted in preventive and/or therapeutic agents for infection comprising a peptide antigen, an antibody, or a vaccine as an active ingredient can be adopted for preparing the preventive and/or therapeutic agent for HIV infection comprising the peptide antigen, the antibody, or the HIV vaccine of the present invention as an active ingredient. For example, dosage forms or adjuvants or additives usually adopted in preventive and/or therapeutic agents for infection comprising a peptide antigen, an antibody, or a vaccine as an active ingredient can be used.

Hereinafter, the present invention will be described more specifically with reference to Reference Examples and Examples. However, the scope of the present invention is not intended to be limited to that of Examples below. The present invention has been achieved by results based on 2008 Grant-in-Aid from the Ministry of Health, Labour and Welfare Japan for Scientific Research Fund (Project of Research on AIDS/HIV).

Reference Example 1

Synthesis of an N36 Peptide Derivative and Confirmation of Antigenicities Thereof (1) Outline of Schemes to Synthesize an N36 Peptide Derivative and Antigen Molecule Before synthesis of a trimer of N36 peptide derivative and confirmation of its antigenicity, it was decided to first confirm the presence or absence of antigenicity of an N36 peptide derivative. This is because the antigenicity may not largely be increased by the trimerization of the N36 peptide derivative if the N36 peptide derivative in a monomeric form does not exhibit any antigenicity. Thus, it was decided to confirm the antigenicities by synthesizing an N36 peptide derivative and immunizing mice therewith. For using peptides as antigen molecules, a method comprising increasing their molecular weights by coupling to a carrier protein such as keyhole limpet hemocyanin (KLH) or a multi antigen peptide (MAP) to thereby enhance antigenicity is known as a method conventionally used. MAP, which permitted convenient synthesis and identification, was used as a carrier this time according to the conventional method, and MAP was also synthesized. The synthesized N36 peptide derivative (antigen molecule) was coupled to this MAP and used in mouse immunization. In this context, all mice used in Reference Examples or Examples of the present application are male BALB/c mice. These mice were purchased from CLEA Japan, Inc., then raised in the animal facility of Tokyo Medical and Dental University, and used in each experiment when they were 6 to 8 week old at the start thereof.

MAP is an immunologically inactive molecule consisting of a radially branched dendrimer of lysine (Lys) residues. The whole molecular weight can be increased by coupling antigen molecules to the end of the MAP molecule. In addition, the antigenicity of antigen molecules can be enhanced by placing a large number of the antigen molecules per MAP molecule. Furthermore, arginine (Arg) and glutamine (Glu) residues were placed at the N terminus of MAP to enhance hydrophilicity (FIG. 7).

Previous research has revealed, as to the MAP-coupling site of the N36 peptide derivative, that a region important for hexamerization is located at the C termini of the N36 peptide derivative (see Non-Patent Documents 12 to 17 in Background Art). Therefore, the N36 peptide derivative was coupled via their N termini to MAP. The antigen molecule of the N36 peptide derivative thus synthesized was used to confirm the antigenicities of the N36 peptide derivative and establish antibody induction experiment and serum evaluation systems using mice. Thus, a peptidic antigen molecule already reported to have the high ability to induce antibodies was first synthesized as a positive control. At the same time, the N36 peptide derivative (hereinafter, also referred to as "NP101") was also synthesized.

The peptide synthesis was performed by Fmoc solid-phase peptide synthesis (Fmoc-SPPS). Its synthesis scheme is shown below (FIG. 8). The solid-phase synthesis method is a method by which the peptides of interest can be synthesized by repeating the procedures of selective deprotection of a protective group 9-fluorenylmethoxycarbonyl (Fmoc) group for the amino group of the principal chain and condensation reaction, finally followed by cleavage from resin and deprotection. In this solid-phase synthesis method, a reaction is performed on an insoluble resin, and all reagents used in the reaction can be washed off. Therefore, the compound of interest can be obtained without the need for purification midway in the method. The peptide synthesis by the solid-phase synthesis method was specifically performed by a method shown below.

Chemical reagents for peptide synthesis including Fmoc-protected amino acids were purchased from Novabiochem, KOKUSAN CHEMICAL CO., LTD., and WATANABE CHEMICAL INDUSTRIES, LTD. An N36 peptide derivative was synthesized using NovaSyn TGR resins. The peptide synthesis was manually performed using side chain-protected amino acids shown below. Meanwhile, monomeric peptides and MAP were prepared using the chemical properties of Fmoc. Each cycle involved (1) deprotection for 15 minutes using 20% by mass of piperidine/DMF, and (2) coupling for 90 minutes using a solution containing 5 equivalents of Fmoc-amino acid (Fmoc-AA-OH), 5 equivalents of HOBt, and 5 equivalents of DIPCI in 2 mL of DMF. As a result of confirming coupling efficiency by a Kaiser ninhydrin test, negative results were obtained, indicating free amino groups less than 0.05%. When slightly positive results were obtained in the Kaiser ninhydrin test, coupling was repeated again. In this case, the coupling was performed using a solution containing 3 equivalents of Fmoc-amino acid (Fmoc-AA-OH), 3 equivalents of HOBt, 3 equivalents of DIPEA, and 2.9 equivalents of HBTU in 2 mL of DMF. When positive results were still obtained in the Kaiser ninhydrin test even after the 2nd coupling, the remaining free amino groups were acetylated (capped) using a mixture of acetic anhydride ($Ac_2O$) and DMF. After the completion of peptide synthesis, the resin was extensively washed with DMF and DCM and dried in a vacuum for 6 hours. The synthesized peptides were separated from the resin using a mixed solution of TFA, thioanisole, ethanedithiol, m-cresol, water, and triisopropylsilane (10:0.75:0.75:0.25:0.25:0.1 (volume ratio)) at room temperature for 90 minutes. The reaction solution was filtered through a filter, and the resin was washed three times with TFA. The filtrate was dehydrated in a vacuum, and peptides were deposited as solid powder by the addition of ethanol. After centrifugation, these procedures from washing with TFA to deposition were repeated 3 times. The obtained peptides were dried in a vacuum for 6 hours. These peptides were purified by RP-HPLC (column: YMC-Pack ODS-A, 10ϕ×250 mm). The HPLC solvents used were water containing 0.1% by mass of TFA (solvent A) and acetonitrile containing 0.1% by mass of TFA (solvent B). All the purified peptides were identified by MALDI-TOF-MS. All the peptides were freeze-dried and then obtained as TFA salts.

(2) Synthesis of NP101

Figure 9:
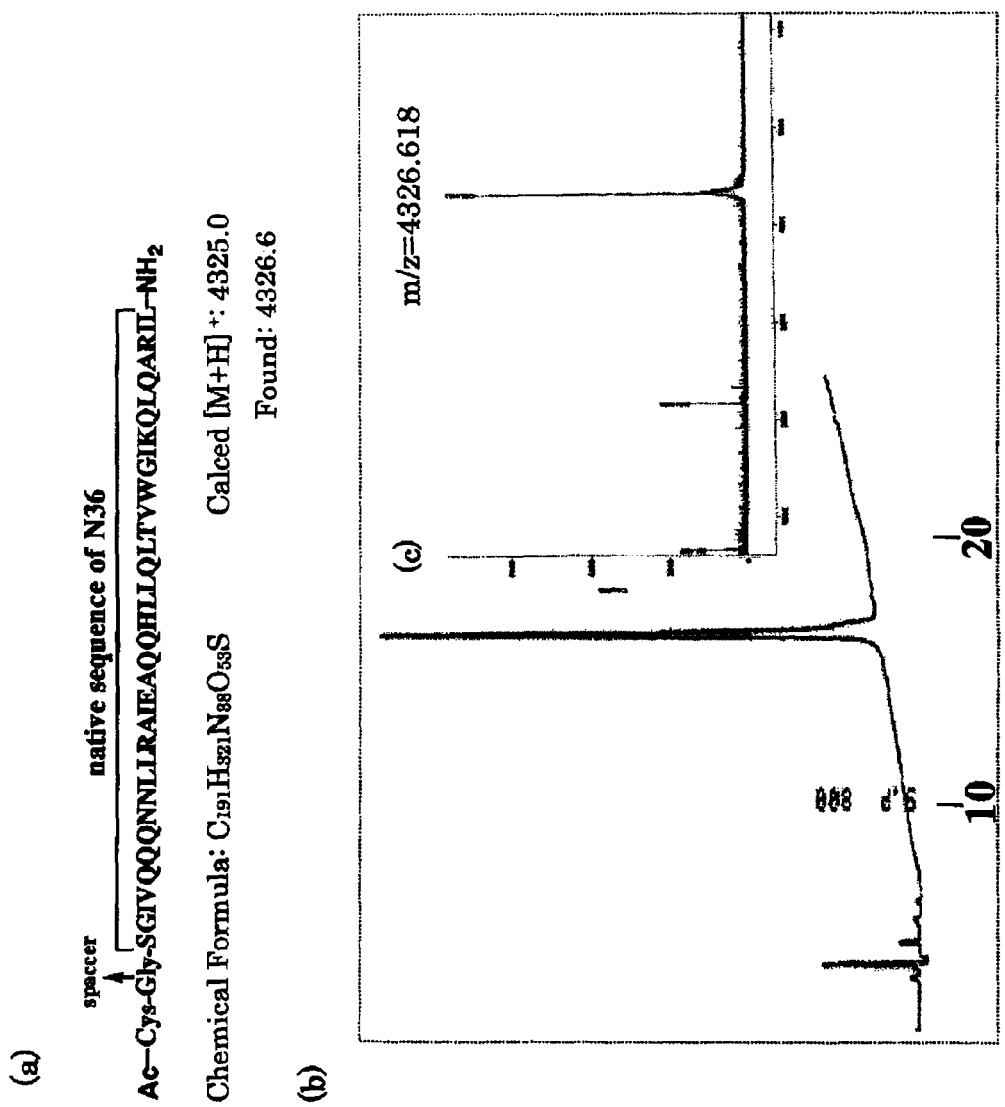
FIG. 9 is a diagram related to the synthesis of NP101.

The structure of NP101 to be synthesized is to which a cysteine residue as a reactive group for subsequent coupling to MAP at N terminus of the native N36 peptide and a glycine (Gly) residue as a spacer between the native N36 peptide and the cysteine (Cys) residue to prevent reduction in reactivity caused by steric hindrance are introduced (FIG. 9(a)). NP101 was synthesized by the Fmoc-SPPS method described above. The obtained reaction solution was subjected to cleavage from resin and deprotection, and then, the peptides were purified by HPLC (high-performance liquid chromatography). In this HPLC, using 5C18-AR-II Waters 4.6×250 mm as a column, 35 to 65% by mass of acetonitrile/water (0.1% by mass of TFA) was flowed as an elution solvent at a flow rate of 1.0 mL/min. for 30 minutes, and detection was carried out at a detection wavelength of 220 nm (FIG. 9(b)). The peptides thus purified by this HPLC were identified by MALDI-TOF MS (matrix-assisted laser desorption/ionization time-of-flight mass spectrometer) (FIG. 9(c)).

The MALDI-TOF MS analysis data of NP101 is shown below.

NP101; m/z calcd for $C_{191}H_{322}N_{38}O_{53}S$ [M+H$^+$]: 4325.0. found: 4326.6.

(3) Synthesis of Positive Control Antigen

Figure 10:
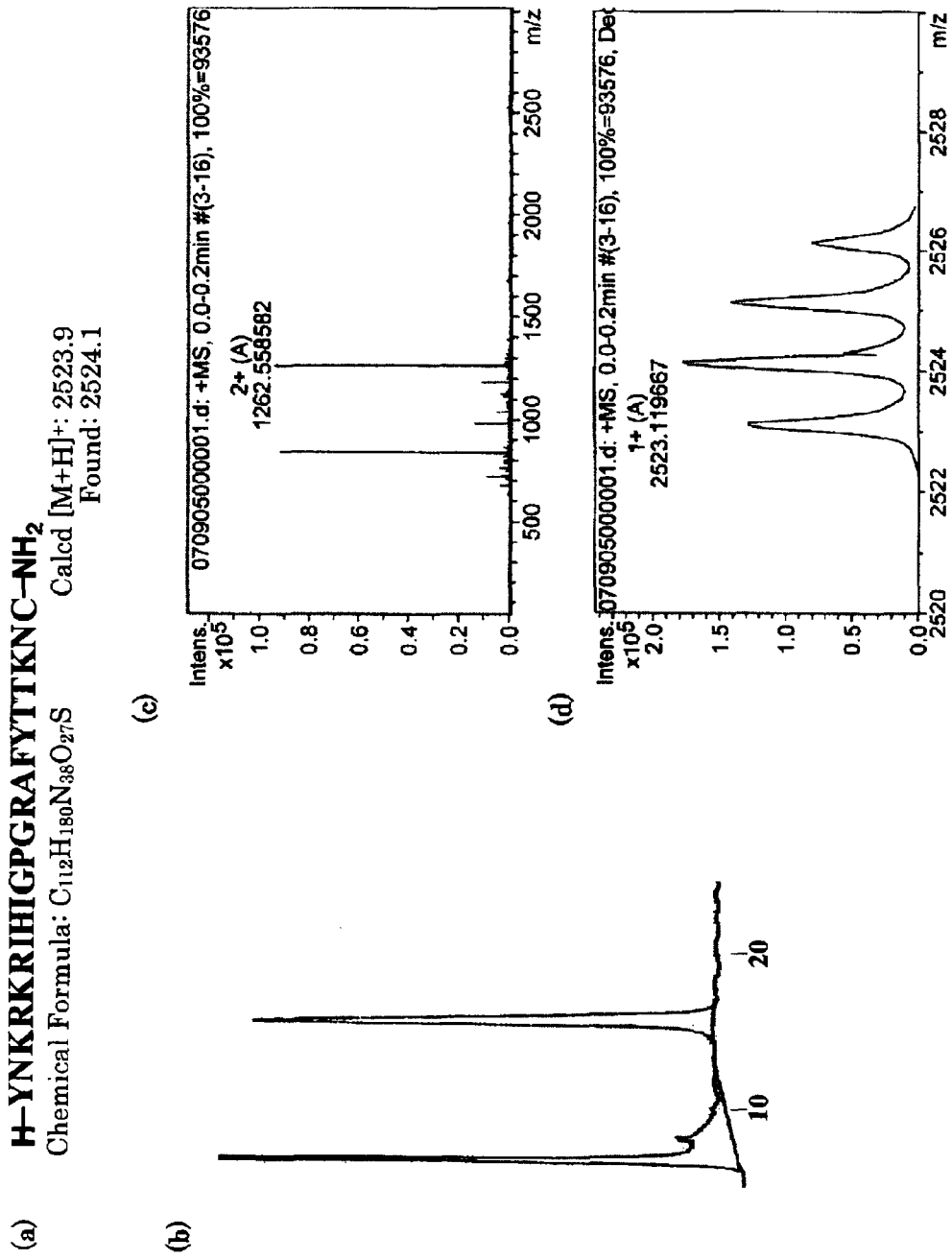
FIG. 10 is a diagram related to the synthesis of a positive control antigen.

A V3 region peptide (FIG. 10(a)), which was already reported to have the high ability to induce antibodies and was a partial peptide of the surface protein gp120 in HIV, was adopted as a positive control antigen in the antibody induction experiment described later. This V3 region peptide is a peptide that serves as a binding site for CXCR4 that binds as a co-receptor during the membrane fusion of HIV. Moreover, this V3 region peptide has a cysteine residue at the C terminus and also has the advantage that the thiol group of the cysteine residue can be used directly for introduction (coupling) to MAP. Furthermore, it has also been reported that antibodies induced from this V3 region peptide have an anti-HIV activity, although this activity is limited to particular HIV strains. The V3 region peptide was synthesized by the Fmoc-SPPS method described above. The obtained reaction solution was subjected to cleavage from resin and deprotection, and then, the peptides were purified by HPLC. In this HPLC, using 5C18-AR-II Waters 4.6×250 mm as a column, 17 to 22% by mass of acetonitrile/water (0.1% by mass of TFA) was flowed as an elution solvent at a flow rate of 1.0 mL/min. for 30 minutes, and detection was carried out at a detection wavelength of 220 nm (FIG. 10(b)). The peptides thus purified by this HPLC were identified by ESI-TOF MS (FIGS. 10(c) and 10(d)). The ESI-TOF MS analysis data of the positive control is shown below.

Positive control; m/z calcd for $C_{112}H_{150}N_{38}O_{27}S$ [M+H$^+$]: 2523.9. found: 2524.1.

(4) Synthesis of MAP

MAP (FIG. 11(a)) was also synthesized, purified, and identified using the same approach as that for the V3 region peptide. Specifically, MAP was synthesized as a radially branched dendrimer of lysine residues by condensing Fmoc- Lys(Fmoc)-OH on a resin. Then, to introduce a chloroacetyl group (which was used in the reaction with the cysteine residue as a coupling partner) to this MAP, the Fmoc groups protecting the amino groups at the N terminus and side chains were removed, and the chloroacetyl group was introduced thereto by a dehydration-condensation reaction using chloroacetic acid, 1-hydroxybenzotriazole (HOBt), and N,N'-diisopropylcarbodiimide (DIPCI). The reaction solution was subjected to cleavage from resin, deprotection, and HPLC purification. In this HPLC, using 5C18-AR-II Waters 4.6×250 mm as a column, 25 to 28% by mass of acetonitrile/water (0.1% by mass of TFA) was flowed as an elution solvent at a flow rate of 1.0 mL/min. for 30 minutes, and detection was carried out at a detection wavelength of 220 nm (FIG. 11(*b*)). The MAP thus purified by this HPLC was identified by ESI-TOF MS (FIG. 11(*c*)) to obtain the MAP of interest. The ESI-TOF MS analysis data of MAP is shown below. MAP; m/z calcd for m/z calcd for $C_{112}H_{18}N_{38}O_{27}S$ [M+H$^+$]: 2097.7. found 2097.0.

(5) Coupling Between MAP and NP101

NP101 synthesized in the paragraph (2) of Reference Example 1 was coupled to MAP synthesized in the paragraph (4) of Reference Example 1. More specifically, a chloroacetyl group was first introduced to MAP, which was then coupled to NP101 using a reaction by which a covalent bond was formed by the nucleophilic attack on MAP by the thiol group of N36 containing the cysteine (Cys) residue introduced at the N terminus. This reaction is often used in the reaction of peptidic compounds because it proceeds in a buffer adjusted to a basic pH, i.e., under mild conditions. The coupling between MAP and NP101 was specifically performed by a method shown below.

MAP (130 μg, 0.06 μmol) and NP101 (4.1 mg, 0.95 μmol) were dissolved under nitrogen conditions in 1 mL of 100 mM PBS (pH 8.5) containing 6 M Gu.HCl, and this solution was stirred at room temperature for 2 days. The resulting reaction was monitored by HPLC and ESI-TOF-MS. At the point in time when no change was seen in the HPLC chart, the reaction was completed, and the reaction solution containing a mixture of all polysubstituted forms was desalted by filtration through Sephadex G-10 using 10% by mass of aqueous acetic acid solution. Then, the filtrate was freeze-dried to prepare an antigen molecule sample (hereinfter, also referred to as an "NP101-MAP antigen molecule") for the antibody induction experiment described later.

Figure 12:
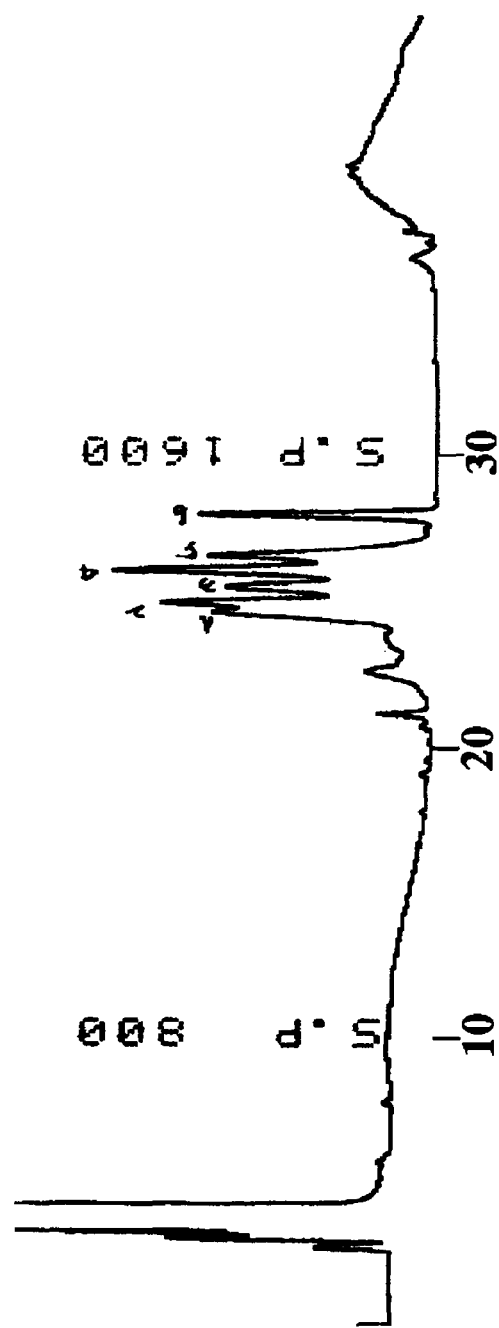
FIG. 12 is a diagram showing an HPLC chart of the coupling reaction between NP101 and MAP.
Figure 13:
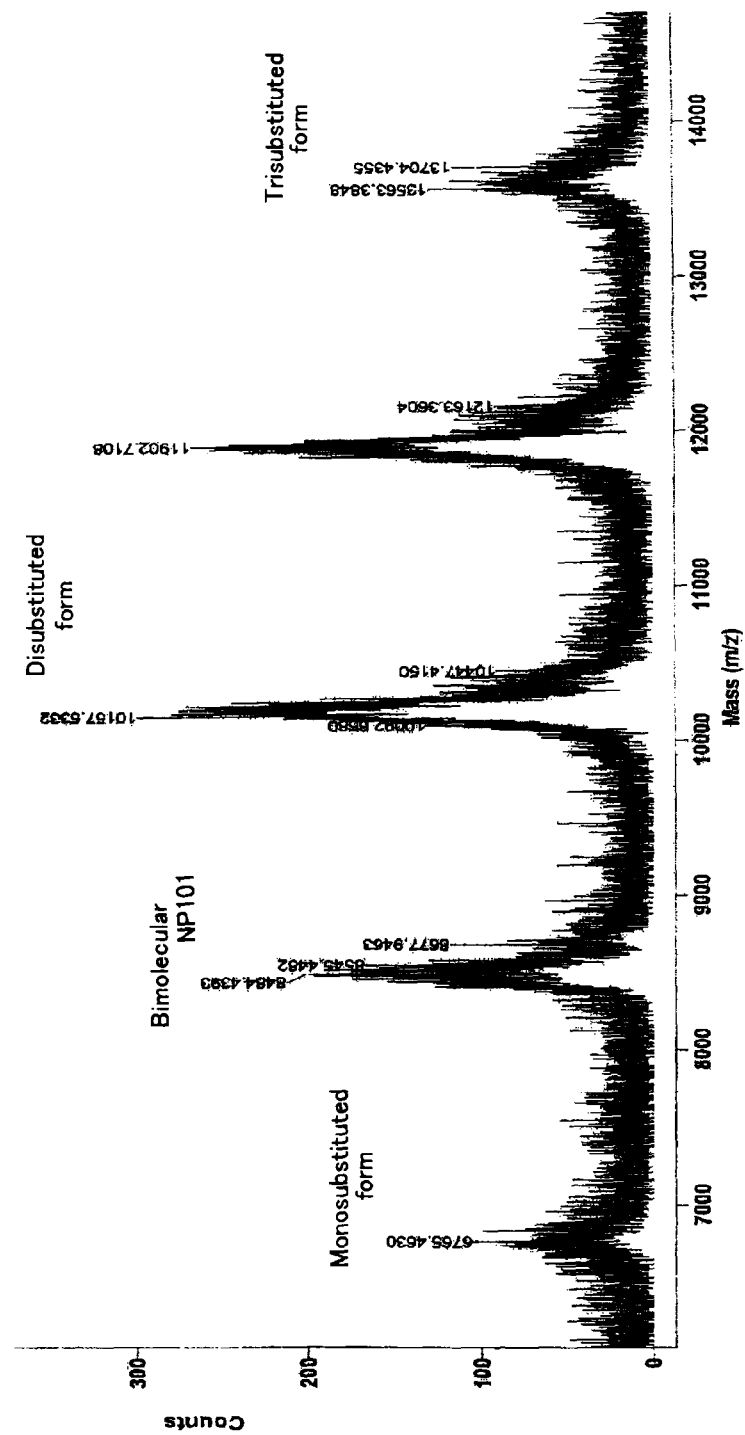
FIG. 13 is a diagram showing results of MALDI-TOF MS of NP101-MAP after HPLC.

Results of an HPLC chart for the NP101-MAP antigen molecule are shown in FIG. 12. In this HPLC, using 5C18-AR-II Waters 4.6×250 mm as a column, 15 to 45% by mass of acetonitrile/water (0.1% by mass of TFA) was flowed as an elution solvent at a flow rate of 1.0 mL/min. for 30 minutes, and detection was carried out at a detection wavelength of 220 nm. Results of identifying, by MALDI-TOF MS, the antigen molecule thus purified by this HPLC are shown in FIG. 13. As is evident from the results of FIG. 13, the formed NP101-MAP antigen molecule contained MAP coupled to one molecule of NP101 (monosubstituted form), MAP coupled to two molecules of NP101 (disubstituted form), and MAP coupled to three molecules of NP101 (trisubstituted form). The Gu.HCl described above is known as a protein denaturant and was also added in this reaction for the purpose of resolving aggregation or insolubility probably caused by the three-dimensional structure of NP101.

(6) Coupling Between MAP and Positive Control Antigen

The positive control antigen synthesized in the paragraph (3) of Reference Example 1 was coupled to MAP in the same way as in the paragraph (5) of Reference Example 1. Specifically, MAP (500 μg, 0.21 μmol) and the positive control (6.36 mg, 2.52 μmol) were dissolved under nitrogen conditions in 500 μL of 100 mM sodium phosphate buffer (pH 8.5) containing 6 M Gu.HCl, and this solution was stirred at room temperature for 6 hours. The resulting reaction was monitored by HPLC and ESI-TOF-MS. At the point in time when polysubstituted forms could be confirmed and no change was seen in the HPLC chart, the reaction was completed, and the reaction solution was desalted by filtration through Sephadex G-10 using 10% by mass of aqueous acetic acid solution. Then, the filtrate was freeze-dried to prepare an antigen molecule sample (hereinafter, also referred to as a "positive control-MAP antigen molecule") for the antibody induction experiment described later.

Figure 14:
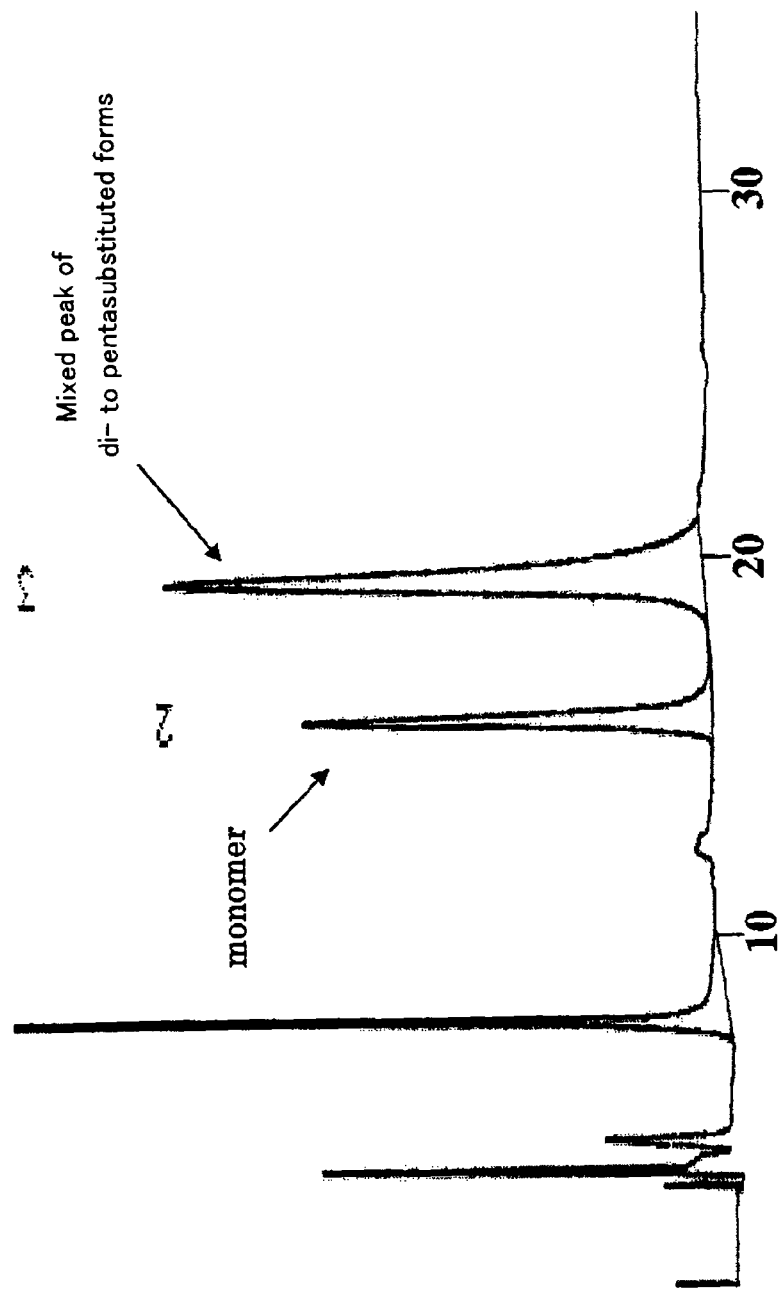
FIG. 14 is a diagram showing an HPLC chart of the coupling reaction between the positive control and MAP.
Figure 15:
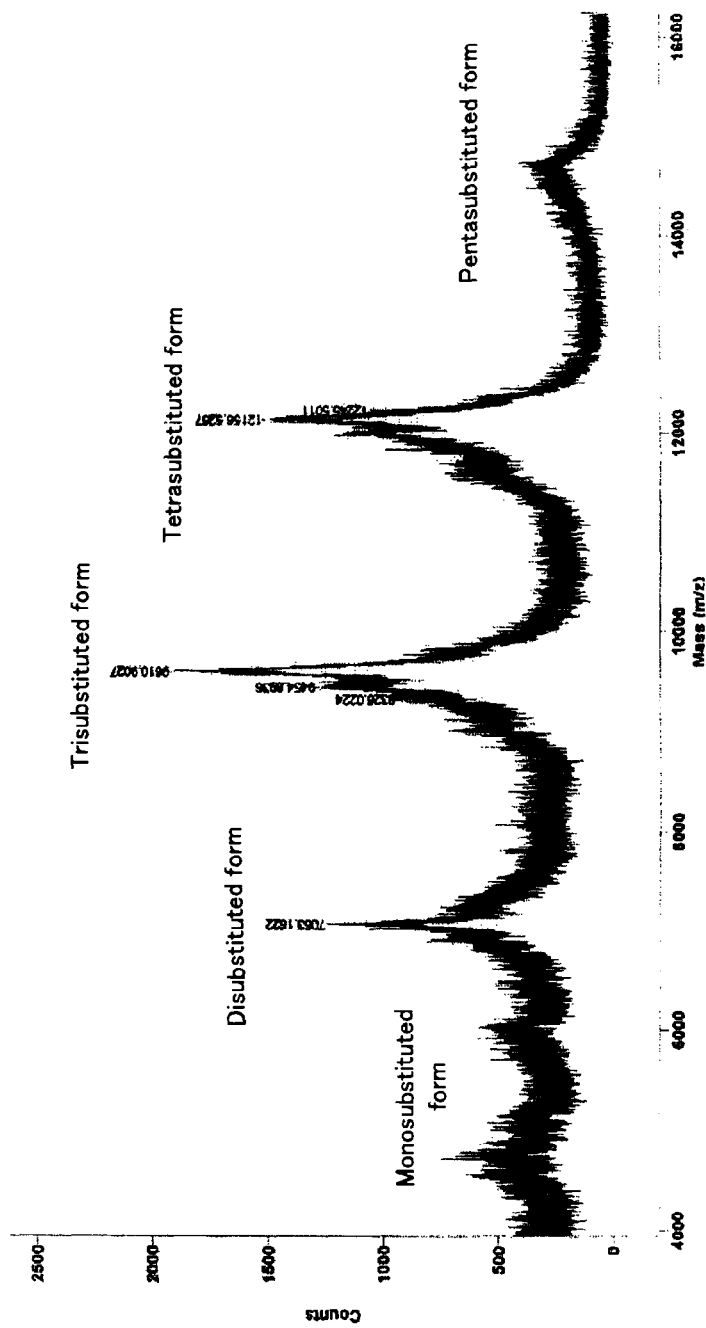
FIG. 15 is a diagram showing results of MALDI-TOF MS of positive control-MAP after HPLC.

Results of an HPLC chart for the positive control-MAP antigen molecule are shown in FIG. 14. In this HPLC, using 5C18-AR-II Waters 4.6×250 mm as a column, 17 to 30% by mass of acetonitrile/water (0.1% by mass of TFA) was flowed as an elution solvent at a flow rate of 1.0 mL/min. for 30 minutes, and detection was carried out at a detection wavelength of 220 nm. Results of identifying, by MALDI-TOF MS, the antigen molecule thus purified by this HPLC are shown in FIG. 15. As is evident from the results of FIG. 15, the formed positive control-MAP antigen molecule contained MAP coupled to one molecule, two molecules, three molecules, four molecules, or five molecules of the positive control antigen (monosubstituted, disubstituted, trisubstituted, tetrasubstituted, and pentasubstituted forms, respectively). In the antigen molecule synthesis, mono- to pentasubstituted forms could be confirmed for positive control-MAP, whereas the reaction for NP101-MAP proceeded merely to form mono- to trisubstituted forms. This may be because reactivity was reduced due to deposition of precipitates probably attributed to the lower solubility of the NP101 itself synthesized for the NP101-MAP synthesis than that of the positive control, and formation of disulfide forms.

Reference Example 2

Antibody Induction Experiment (1) Outline of Scheme of Antibody Induction Experiment For evaluating the ability to induce antibodies, an antibody induction experimental system using mice was used as a general experimental system conventionally used. The mice used were 6-week-old mice of BALB/c lineage. The reason for using the mice of this lineage was that fusion between the same species is achieved by using BALB/c mouse-derived myeloma cells in monoclonal antibody preparation and this approach is generally used as a hybridoma preparation method (See Lidqvist, M., Nilsson, O., Holmgren, J., Hall, C., Fermer, C. Phage display for site-specific immunization and characterization of high-risk human papillomavirus specific E7 monoclonal antibodies. J. Immune. Meth. 337, 88-96 (2008)).

Use of a mixture of antigen molecules with adjuvants produces the effect of potentiating immunogenicity and slowing down the metabolic rate of the antigen molecules in vivo and therefore allows stimulation of the mouse immune system over a longer period. Thus, adjuvants were used in the antibody induction experiments of this Reference Example or Examples. Moreover, adjuvants usually used are divided into two types: incomplete and complete adjuvants. Either of these adjuvants is made of mineral oil as the principal material. The complete adjuvant further comprises killed *Mycobacterium tuberculosis*, in addition to the mineral oil, and can allegedly be expected to have a higher immunogenicity-potentiating effect. However, a Freund's incomplete adjuvant, one kind of incomplete adjuvant, was used in this Reference Example or Examples with reference to the procedures of previously performed antibody induction experiments using peptidic antigen molecules.

The dose of the antigen molecule used in each challenge in the immunization of the mice, an administration method, and the immunization schedule were set as described below with reference to the procedures of previously performed antibody induction experiments (FIG. 16) (See Roberts, W. K., Livingston, P. O., Agus, D. B., Ibarz, J. P., Scheinberg, Z. A. Vaccination with CD20 peptides induces a biologically active, specific immune response in mice. Blood 99, 3748-3755 (2002); Kutzler, M. K., Cao, C., Bai, Y., Dong, H. Q., Choe, P. Y., Saulino, V., McLaughlin, L., Whelan, A., Chooa, A. Y., David, B. Weiner D. B., Ugenc, K. E. Mapping of immune responses following wild-type and mutant ABeta42 plasmid or peptide vaccination in different mouse haplotypes and HLA Class II transgenic mice. Vaccine 24, 4630-4639 (2006); Vancott, T. C., Mascola, J. R., Kaminski, R. W, Birx, D. L. Antibodyes with specificity to native gp120 and neutralization activity against primary human immunodeficiency virus type 1 isolates elicited by immunization with oligomerric gp160. J. Virol. 71, 4319-4330 (1997); Burton, D. R., Desrosiers, R. C., Doms, R. W., Koff, W. C., Kwong, P. D., Moore, J. P., Nabel, G. J., Sodroski, J., Wilson, I. A., Wyatt, R. T. HIV vaccine design and the neutralizing antibody problem. Nat. Immunol. 5, 233-236 (2004)).

Figure 16:
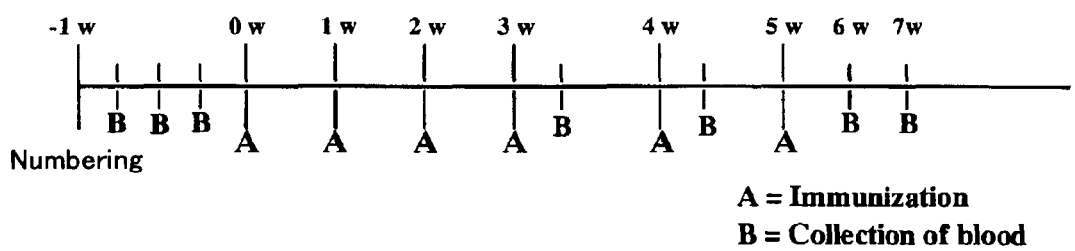
FIG. 16 is a diagram showing the schedule of immunization and collection of blood in an antibody induction experiment.

Each antigen molecule for immunization was dissolved in DMSO (dimethyl sulfoxide) or $H_2O$ to prepare a stock solution. Specifically, an "NP101-MAP antigen molecule stock solution" containing 4 mg of NP101-MAP dissolved in 100 μL of solvent ($H_2O$:DMSO solution=1:1 (volume ratio)) and a "positive control-MAP antigen molecule stock, solution" containing 2 mg of the positive control antigen dissolved in 200 μL of solvent ($H_2O$) were prepared. 100 μL of adjuvant solution (50 μL of adjuvant+50 μL of PBS) was added to an aliquot of 100 μg of each of these stock solutions and mixed to prepare emulsions for immunization. In this context, since DMSO might exhibit toxicity, the final concentration of DMSO was set to 1% by mass or less in these emulsions for immunization. Moreover, DMSO was added at a final concentration of 1% by mass to an antigen molecule-free adjuvant solution (adjuvant:PBS=1:1 (volume ratio)) to prepare an emulsion for immunization as a negative control. Subsequently, 6-week-old mice of BALB/c lineage anesthetized with diethyl ether were immunized by the subcutaneous injection of these emulsions for immunization. The number of the immunized mice was 4 for the NP101-MAP antigen molecule, 4 for the positive control-MAP antigen molecule, and 3 for the negative control. In this context, a portion of the ears of these mice was excised for differentiating each emulsion for immunization from the other emulsions. Collection of blood from the thus-immunized mice was performed at 1-week intervals using a method by which blood was collected from the orbital floor under anesthesia with diethyl ether. The schedule of such immunization and collection of blood is shown in FIG. 16. The obtained blood was separated into serum and clot by centrifugation. Only the serum fraction was collected, cryopreserved at −80° C., and used by thawing when needed in the experiment.

(2) Evaluation of Antibody Titer by ELISA

ELISA (Enzyme-Linked Immunosorbent Assay) method (Godefroy, S., Peyre, M., Garcia, N., Muller, S., Sesardic, D., Partidos, C. D. Effect of skin barrier disruption on immune responses to topically applied cross-reacting material, CRM197, of diphtheria toxin Infect. Immin. 73, 4803-4809 (2005); Albu, D. I., Trower, A. J., Woron, A. M., Stellrecht, K., Broder, C. C., Metzger, D. W. Intranasal vaccination using interleukin-12 and cholera toxin subunit B as adjuvants to enhance mucosal and systemic immunity to human immunodeficiency virus type 1 glycoproteins. J. Virol. 77, 5589-5597 (2003)) was adopted as a system for evaluating the antibody titer of the serum obtained in the paragraph (1) of Reference Example 2. Specifically, the evaluation was performed by a method shown below.

First, reagents were prepared. Tween (polyoxyethylene (20) sorbitan monolaurate) and 30% by mass of aqueous hydrogen peroxide solution were purchased from Wako Pure Chemical Industries, Ltd. Skim milk for a blocking buffer was purchased from Snow Brand Milk Products Co., Ltd. ABTS ((2,2-azino-bis(3-ethylbenzothiazoline-6-sulfonic acid)diammonium salt) was purchased from Sigma-Aldrich Corp. HRP-labeled goat anti-mouse IgG (H+L) was purchased from NOVAGEN. 96-well Half Area Plate-Flat-High Bind (microplate) was purchased from Corning, Inc.

To adsorb the antigen molecule (NP101-MAP antigen molecule or positive control-MAP antigen molecule) onto the microplate, this microplate was coated overnight at 4° C. with 25 μL of synthetic peptide in 10 μg/mL PBS. The coated microplate was washed 10 times with deionized water and blocked at 37° C. for 1 hour with 150 μL of blocking buffer (0.02% by mass of PBST containing 5% by mass of skim milk). This microplate was washed with deionized water. Each serum (serum obtained from the mice immunized with each antigen molecule) obtained in the paragraph (1) of Reference Example 2 was diluted with 1% by mass of skim milk containing 0.02% by mass of PBST to prepare 201-fold, 401-fold, 801-fold, and 102400-fold diluted solutions for each serum. 50 μL each of the diluted solutions was added to the microplate and incubated at 37° C. for 2 hours. All steps subsequent thereto were performed at room temperature. The microplate was washed 10 times with deionized water. A solution of an HRP (horseradish peroxidase)-labeled anti-mouse IgG antibody (secondary antibody) diluted 2001-fold with 0.02% by mass of PBST was added in a sufficient amount to the solution (25 μL) in each well of the microplate and incubated for 45 minutes. Then, the wells of the microplate were washed 10 times, and an HRP substrate solution was added thereto at a concentration of 25 μL/well. This HRP substrate solution was a solution prepared by adding 10 mg of ABTS (2,2'-azino-bis(3-ethylbenzothiazoline-6-sulfonic acid) to 200 μL of HRP-staining buffer (1 mL of 0.5 M citrate buffer (pH 4), 3 μL of hydrogen peroxide, and 8.8 mL of water) containing 0.02% by mass of PBST. After incubation for 30 minutes from the addition of the HRP substrate solution, the reaction was terminated by the addition of 0.5 M sulfuric acid at a concentration of 25 μL/well, and OD of the solution was measured at 405 nm.

The antibody titer of the obtained serum was measured by these procedures. The results are shown in FIG. 17. FIG. 17(a) shows results of ELISA using the "NP101-MAP-immobilized plate" and the "serum obtained by the administration of the negative control"; FIG. 17(b) shows results of ELISA using the "NP101-MAP-immobilized plate" and the "serum obtained by the administration of NP101-MAP"; and FIG. 17(c) shows results of ELISA using the "positive control-MAP-immobilized plate" and the "serum obtained by the administration of positive control-MAP". In FIG. 17, "d" means the number of lapsed days from the initial immunization day (0 d). For example, 20 d means 20 days after the initial immunization day, while −7 d means 7 days before the initial immunization day.

As is evident from the results of FIG. 17(a), the antibody titer of the serum induced with the negative control for NP101-MAP was the same as that of the serum collected before immunization, showing no rise in antibody titer for NP101-MAP.

Moreover, as is evident from the results of FIG. 17(b), a gradual rise could be confirmed in the antibody titer of the serum induced with NP101-MAP, for NP101-MAP. Furthermore, on 43 d (43 days after the initial immunization), the serum induced by immunization with positive control-MAP merely exhibited the activity similar to that of the serum before immunization. These results demonstrated that the serum obtained by immunization with NP101-MAP specifically recognized NP101.

On the other hand, as is evident from the results of FIG. 17(c), a gradual rise could be confirmed in the antibody titer of the serum induced with positive control-MAP, for positive control-MAP. Furthermore, on 43 d (43 days after the initial immunization), the serum induced by immunization with NP101-MAP merely exhibited the activity similar to that of the serum before immunization. These results demonstrated that the serum obtained by immunization with positive control-MAP specifically recognized the positive control.

The results described above demonstrated that the antibody induction experimental system using mice functioned and further demonstrated that the monomeric N36 peptide derivative NP101-MAP had a sufficient antibody-inducing effect even compared with the positive control (FIGS. 17(b) and 17(c)). For this reason, it was expected that an N36 peptide trimer would also exhibit antigenicity.

Example 1

Synthesis of N36 Peptide Trimer (1) Design of Antigen Molecule

The results of the experiment of Reference Example 2 could demonstrate that the N36 peptide had antigenicity and demonstrate that the antibody induction experimental system and ELISA normally functioned. Thus, for the original purpose, an attempt was made to synthesize a gp41-mimicking peptide (hereinafter, also referred to as "NP104") by trimerization of N36 peptide derivative. However, from the course of NP101-MAP synthesis, NP104 of interest was presumed to be difficult to synthesize and purify, for example, on the ground that NP101 was low soluble under basic conditions and disulfide formation proceeded. Thus, in the trimerization, a thiazolidine ligation reaction was used, which has previously been reported as a reaction by which a covalent bond can be formed under acidic conditions which are considered to hardly form disulfide bonds and enhance solubility (Tam, J. P., Yu, Q., Lu, Y-A. Tandem peptide ligation for synthetic and natural biological. Biologicals 29, 189-196 (2001); Tam, J. P., Xu, J., Eom, K. D. Methods and strategies of peptide ligation. Biopolymers 60, 194-205 (2001); Liu, C.-A., Tam, J. P. Peptide segment ligation strategy without use of protecting groups. Proc. Natl. Acad. Sci. U.S.A. 91, 6584-6588 (1994); Tam, J. P., Yu, Q., Yang, J.-L. Tandem ligation of unprotected peptides through thiaprolyl and cysteinyl bonds in water. J. Am. Chem. Soc. 123, 2487-2494 (2001); Sadler, K., Zhang, Y., Xu, J., Yu, Q., Tam, J. P. Quaternary protein mimetics of gp41 elicit newtralizing antibodies against HIV fusion-active intermediate state. Biopolymers 90, 320-329 (2008); Miao, Z., Tam, J. P. Bidirectional tandem pseudoproline ligations of proline-rich helical peptides. J. Am. Chem. Soc. 122, 4253-4260 (2000); Eom, K. D., Miao, Z., Yang, J.-L., Tam, J. P. Tandem ligation multipartite peptide with cell-permeable activity. J. Am. Chem. Soc. 125, 73-82 (2002); Tam, J. P., Miao, Z. Stereospecific pseudoproline ligation of N-terminal serine, threonine, or cysteine-containing unprotected peptides. J. Am. Chem. Soc. 121, 9013-9022 (1999)).

Figure 18:
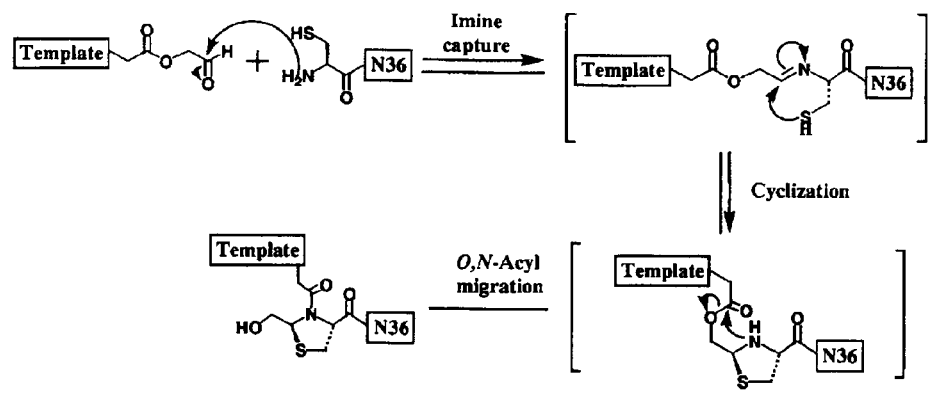
FIG. 18 is a diagram showing the scheme of thiazolidine ligation.

The thiazolidine ligation is a method by which unprotected peptide fragments are ligated to each other via a pseudoproline structure. In this reaction, the amino group of an N-terminal cysteine residue in one peptide initiates the nucleophilic attack on a carbonyl carbon atom in the other peptide having a C-terminal peptidyl glycolaldehyde ester to form imine via which the peptides are ligated to each other. Subsequently, thiazolidine ring formation takes place by the intramolecular nucleophilic attack by the thiol group in the side chain of cysteine within the molecule of the ligated peptides. Through this series of reactions, thiazolidine ester is formed. Then, an O,N-acyl migration reaction can occur to thereby form a stable pseudoproline bond (FIG. 18). Many methods for ligation based on this pseudoproline bond have been developed so far. It is known that even a tryptophan, serine, threonine, histidine, or asparagine residue used instead of the cysteine residue assumes a similar structure for ligation. Among them, the cysteine residue has been reported to produce particularly high reactivity and high yields of peptide conjugates (Tam, J. P., Miao, Z. Stereospecific pseudoproline ligation of N-terminal serine, threonine, or cysteine-containing unprotected peptides. J. Am. Chem. Soc. 121, 9013-9022 (1999)). In the thiazolidine ligation reaction, racemic mixtures are formed. However, it was concluded that either R or S form of the antigen molecule of interest had no influence on antibody induction this time. This is because either R or S form can be used without problems in trimerization that is important for antibody induction and the site of this pseudoproline bond is not contained in the recognition site of the antibody of interest. Furthermore, this thiazolidine ligation reaction occurs in a buffer adjusted to within a pH range of 4 to 6, i.e., under mild conditions, and proceeds even in a buffer reduced by mixing with tris(2-carboxyethyl)phosphine hydrochloride (TCEP). Thus, the formation of disulfide bonds between cysteine residues can also be prevented.

(2) Redesign and Synthesis of Monomeric N36 Peptide Derivatives (NP102 and NP103)

Figure 19:
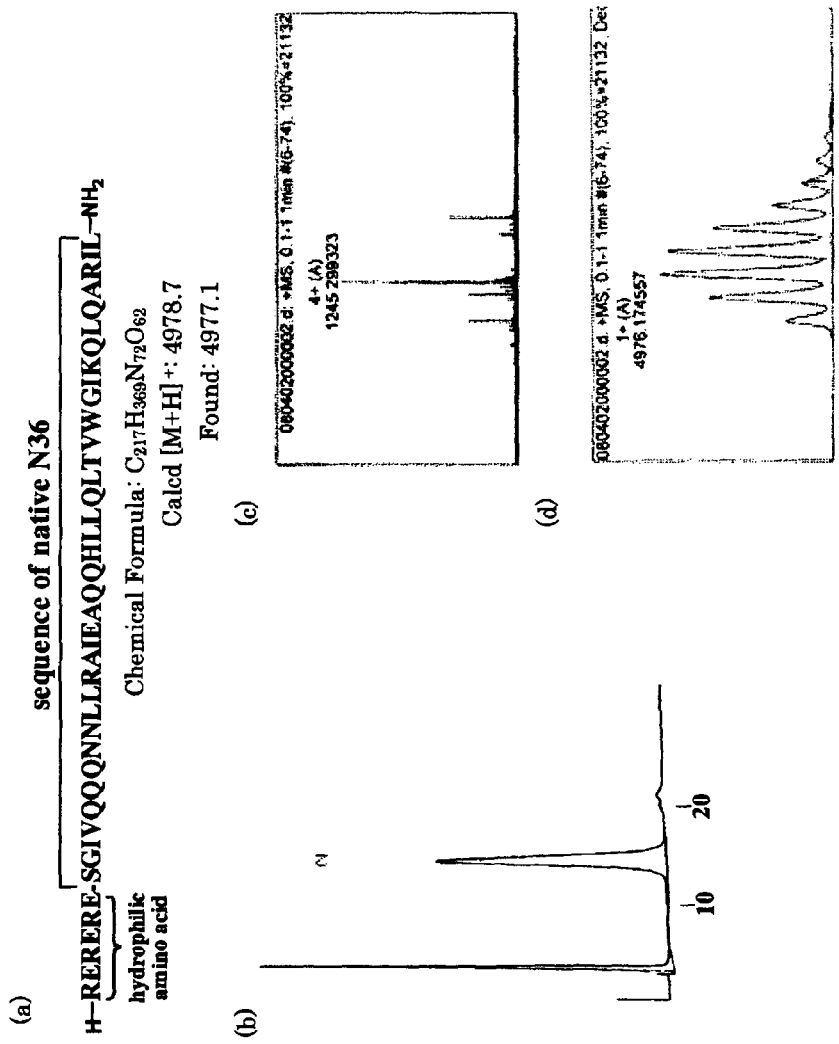
FIG. 19 is a diagram related to the synthesis of NP102.

Monomeric N36 peptide derivatives were redesigned and synthesized. In the same way as the method described in Reference Example 1, peptides comprising a total of 6 residues of hydrophilic amino acids arginine (Arg; R) and glutamic acid (Glu; E) (for enhancing the water solubility) added to N terminus of the native sequence (hereinafter, these peptides are also referred to as "NP102") were synthesized as the monomeric. N36 peptides for constituting NP104 of interest (FIG. 19). FIG. 19(a) shows the amino acid sequence of NP102; and FIG. 19(b) shows an HPLC chart after purification of NP102. In this HPLC, 5C18-AR-II Waters 4.6×250 mm was used as a column, 37 to 47% by mass of acetonitrile/water (0.1% by mass of TFA) was flowed as an elution solvent at a flow rate of 1.0 mL/min. for 30 minutes, and the detection was carried out at a detection wavelength of 220 nm. Results of identifying, by ESI-TOF-MS, the peptides thus purified by this HPLC are shown in FIGS. 19(c) and 19(d). The ESI-TOF MS analysis data of NP102 is shown below. NP102; m/z calcd for $C_{217}H_{370}N_{72}O_{62}[M+H^+]$: 4978.7. found 4977.1.

Figure 20:
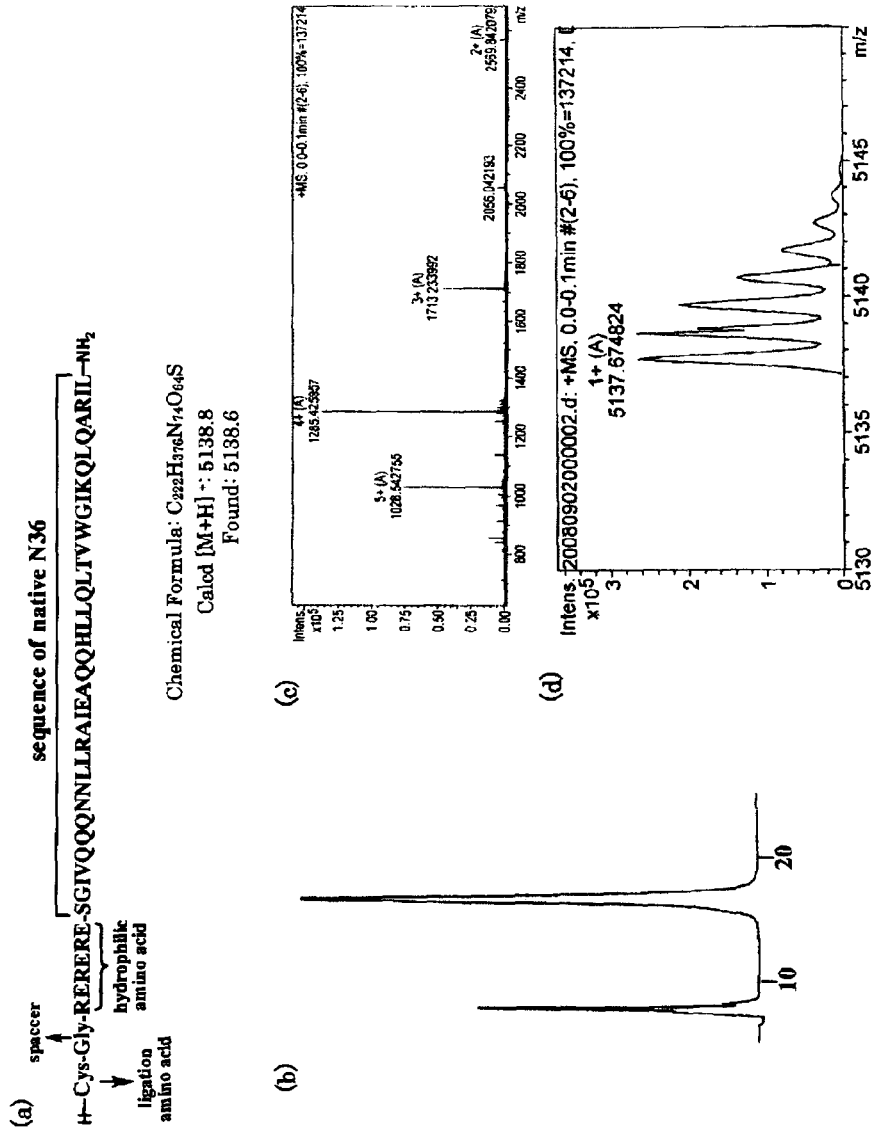
FIG. 20 is a diagram related to the synthesis of NP103.

Next, peptides comprising cysteine (Cys) (which was used in the thiazolidine ligation reaction) further placed at the N terminus of this NP102 and glycine (Gly) placed as a spacer between the cysteine and arginine residues to prevent reduction in reactivity caused by steric hindrance (hereinafter, these peptides also referred to as "NP103") were synthesized in the same way as the method described in Reference Example 1 (FIG. 20). FIG. 20(a) shows the amino acid sequence of NP103. In this HPLC, 5C18-AR-II Waters 4.6×

250 mm was used as a column, 37 to 47% by mass of acetonitrile/water (0.1% by mass of TFA) was flowed as an elution solvent at a flow rate of 1.0 mL/min. for 30 minutes, and the detection was carried out at a detection wavelength of 220 nm. Results of identifying, by ESI-TOF-MS, the peptides thus purified by this HPLC are shown in FIGS. 20(*c*) and 20(*d*). The ESI-TOF MS analysis data of NP103 is shown below.

NP103; m/z calcd for $C_{222}H_{377}N_{74}O_{64}S$ [M+H$^+$]: 5138.89. found 5138.68.

(3) Design and Synthesis of Template Compound

Figure 21:
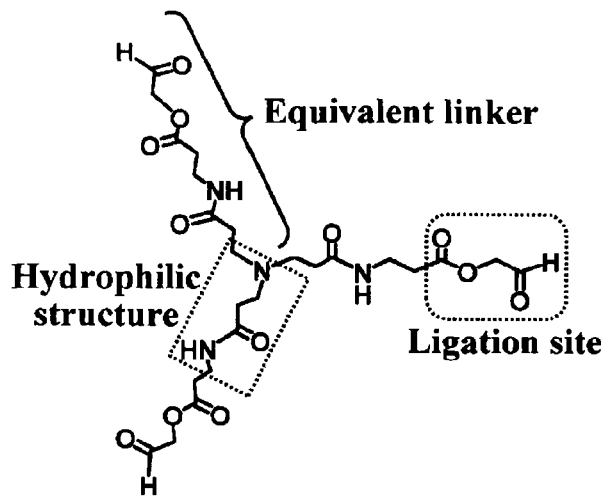
FIG. 21 is a diagram showing the structure of a template compound.
Figure 23:
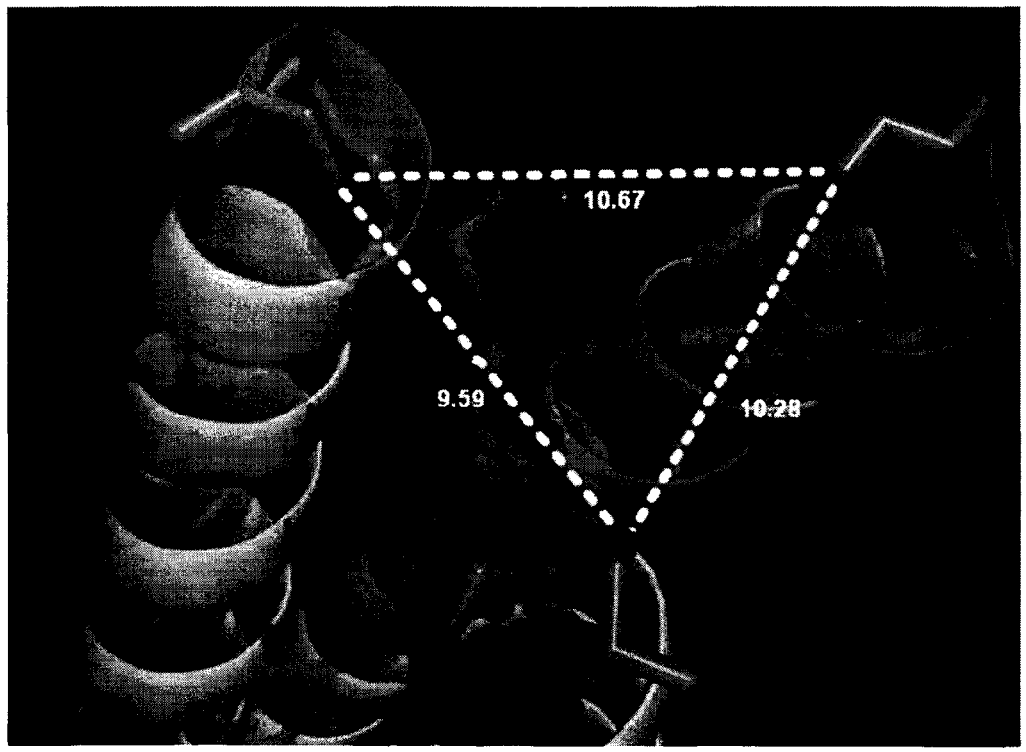
FIG. 23 is a diagram showing the presumed distance between the —SH groups of cysteine residues in added amino acid sequences at the N termini of N36 derivative.

The antigen molecule of final interest in preparation has a trimeric structure obtained by immobilizing, through covalent bonds, an N-terminal helical region of gp41 (N36 peptide). Thus, the structure of the template compound serving as a scaffold for trimerization of the N36 peptide derivative was designed to have three equivalent linkers and C3 symmetry (FIG. 21). Therefore, a "compound 5" (see FIG. 22) having three symmetric bonds extended from the nitrogen atom as a center was used as a starting material to further extend the equivalent linkers. Amide and ester bonds rather than carbon chains were adopted for the three linker moieties. The amide bond has the advantage that it permits easy synthesis and enhances hydrophilicity and detection can be performed at the same wavelength as that for the N36-derived peptides in HPLC for the coupling of the peptides to the template compound. The ester bond and terminal aldehyde in the linker moieties are required for forming a thiazolidine ligation ring for the coupling of the N36 peptides to the template compound. Moreover, it was expected that use of the nitrogen atom as a center would form a quaternary ammonium salt in an acetate buffer (pH 5.2, weakly acidic), which was a ligation reaction condition, to thereby enhance water solubility. Moreover, since information on linker lengths has been obtained by the X-ray crystal structure analysis of the trimeric structure of gp41, the length of each linker was set to a length that seemed to be appropriate with reference to the information (FIGS. 21 and 23). The template compound was specifically synthesized by a method shown below according to the scheme shown in FIG. 22. Hereinafter, each compound will also be denominated according to the description of FIG. 22.

(2) Compound 2

A catalytic amount of iodine was added to a solution containing 1,2,3-propanetriol (1.84 g, 20 mmol) in 20 mL of acetone, and this solution was stirred at room temperature for 15 hours. The reaction was terminated using saturated sulfuric acid and salt water. Subsequently, iodine was removed using sodium dithionite ($Na_2S_2O_4$). An oil residue was obtained by concentration under reduced pressure, and this residue was purified by silica gel chromatography using trichloromethane/methanol (40:1 (volume ratio)) to obtain 1.88 g (14.23 mmol) of compound 2 (yield: 71%). The identification data of this compound 2 is as follows:

$^1$H-NMR (400 MHz; $CD_3OD$) δ=1.37 (3H,s), 1.44 (1H,s), 3.58-3.63 (1H, m), 3.71-3.82 (2H, m), 4.03-4.06 (1H, m), 4.22-4.27 (1H, m)

(b) Compound 4

50 mL of benzyl alcohol and 22.83 mg (120 mmol; 1.2 equivalents) of p-toluene sulfonic acid monohydrate were added to a suspension containing 8.91 g (100 mmol) of β-alanine (compound 3) suspended in 150 mL of toluene, and this solution was stirred at 125° C. for 24 hours using a Dean-Stark trap. This solution was cooled to room temperature and concentrated under reduced pressure. To the residue, 400 mL of diethyl ether was added, and this solution was filtered to collect deposits. The deposits were washed with diethyl ether. The deposits were dried in a vacuum to obtain a compound 4 as 35 g of white solid, which was used without being further purified.

(c) Compound 6

522 mg (3.6 mmol) of $HOBt.H_2O$, 688 mg (3.6 mmol) of EDCI.HCl, 1.315 g (3.6 mmol) of compound 4, and 2.1 mL (15 mmol) of triethylamine ($NEt_3$) were added to 20 mL of dried DMF containing 233 mg (1 mmol) of compound 5, and this solution was stirred at room temperature for 15 hours. The solution was diluted with ethyl acetate. The organic phase was washed with saturated sodium bicarbonate and salt water and then dried over magnesium sulfate. This solution was concentrated under reduced pressure to obtain a residue. The identification data of this compound 6 is as follows:

$^1$H-NMR (400 MHz; $CD_3OD$) δ=2.24 (6H, t, J=6.0 Hz), 2.55 (6H, t, J=6.23 Hz), 2.59-2.62 (6H, m), 3.43-3.48 (6H, m), 5.11 (6H,s), 6.81 (3H, t, J=5.79 Hz), 7.30-7.38 (15H, m). FABLRMS, m/z calcd for $C_{39}H_{49}N_4O_9S$ [M+H$^+$]: 717.83. found: 717.

(d) Compound 7

A catalytic amount of Pd/C (10% by mass) was added into 2 mL of methanol containing 129 mg (0.17 mmol) of compound 6 at room temperature under hydrogen conditions. 5 hours later, this solution was filtered through celite. The filtrate was concentrated under reduced pressure, and the residue was dissolved in 4 mL of dichloromethane. To the solution, 101.1 mg (0.765 mmol) of compound 2, 146.7 mg (0.765 mmol) of EDCI (1-ethyl-3-(3-dimethylaminopropyl)carbodiimide).HCl, and a catalytid amount of DMAP were added, and this solution was stirred at room temperature. 30 minutes later, the solution was concentrated under reduced pressure to obtain a residue. The residue was purified by silica gel chromatography using trichloromethane/methanol (17:1 (volume ratio)) to obtain 90.1 mg (0.114 mmol) of compound 7 (yield: 67%). The identification data of this compound 7 is as follows:

$^1$H-NMR (400 MHz; $CD_3OD$) δ=1.36 (9H,s), 1.44 (9H,s), 2.28-2.31 (12H, t, J=5.94 Hz), 2.53-2.60 (6H, m), 2.65-2.68 (6H, t, J=5.97 Hz), 3.46-3.5 (6H, m), 3.7 (6H,s), 3.74-3.78 (3H, m), 4.07-4.20 (6H, m), 4.31-4.35 (3H, m). FABLRMS, m/z calcd for $C_{36}H_{61}N_4O_{15}$[M+H$^+$]: 789.89. found: 789.

(e) Compound 8 (Template Compound of the Present Invention)

1 mL of methanol:TFA (1:4 (volume ratio)) solution containing 26.3 mg (0.033 mmol) of compound 7 was stirred at room temperature for 2 hours. This solution was concentrated by vaporization, and the residue was dissolved in 1 mL of water:methanol (1:3 (volume ratio)) solution. To this solution, 42.78 mg (0.2 mmol) of $NaIO_4$ was added, and the solution was stirred at room temperature for 1 hour. This solution was concentrated by vaporization. Then, the residue was purified by RP-HPLC (column: YMC-Pack ODS-A, 10ϕ×250 mm). The HPLC solvents used were water containing 0.1% by mass of TFA (solvent A) and acetonitrile containing 0.1% by mass of TFA (solvent B). The purified compound 8 was identified by ESI-TOF-MS. The compound 8 was further purified using a linear gradient of 0 to 15% by mass of the solvent B for 30 minutes or longer. The purified compound 8 was freeze-dried to obtain 7.9 mg (0.014 mmol) of compound 8 (template compound of the present invention: compound represented by the general formula (1) wherein X is 1) (yield: 42%). The identification data of this compound 8 is as follows:

$^1$H-NMR (400 MHz; $D_2O$) δ=2.54-2.54 (6H, m), 2.66 (6H, m), 3.32-3.36 (12H, m), 3.95-3.96 (4H, m), 5.10-5.11 (2H, m). m/z calcd for $C_{24}H_{43}N_4O_{15}$ (M+3H$_2$O$^+$): 627.6. found: 627.8.

(4) Synthesis of NP104 (Trimer of N36 Peptide Derivative)

Figure 24:
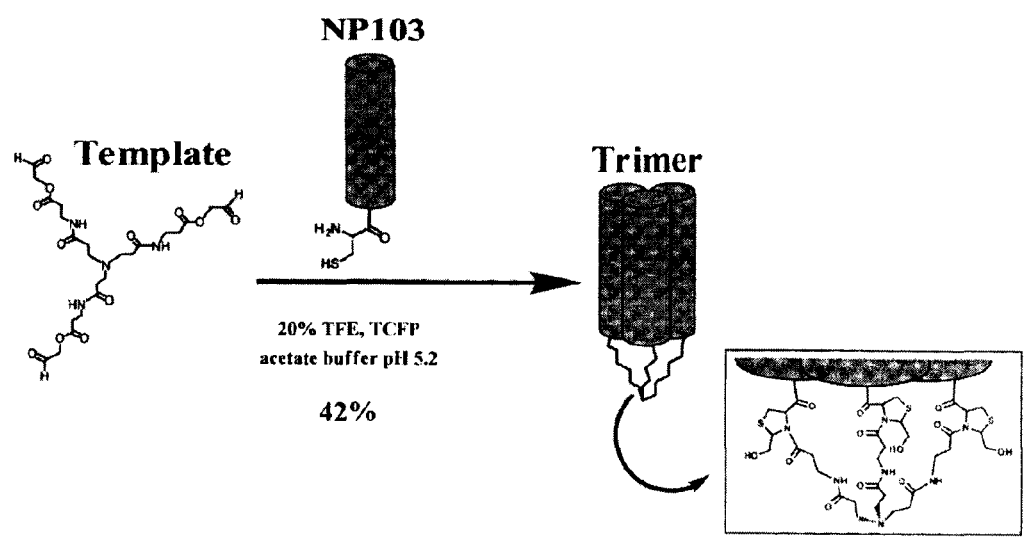
FIG. 24 is a diagram related to a scheme to synthesize NP104. In the diagram, "Template" represents the template compound of the present invention.

An attempt was made to synthesize an N36 peptide trimer using the N36 peptide derivative (NP103) and the template compound. Specifically, NP103 synthesized in the paragraph (2) of Example 1 and the template compound synthesized in the paragraph (3) of Example 1 were stirred in 200 mM acetate buffer (pH 5.2) containing 20% 2,2,2-trifluoroethanol (TFE) to construct a trimer (hereinafter, also referred to as "NP104") comprising 3 molecules of NP103 ligated to the template compound (FIG. 24). Specifically, the synthesis was performed by a method shown below.

100 μg (0.174 μmol) of compound 8 and 3.4 mg (0.574 μmol) of NP103 were dissolved in 300 μL of 200 mM acetate buffer (pH 5.2) and 300 μL of TFE under nitrogen conditions. Subsequently, TCEP.HCl was added to the solution. This solution was stirred at room temperature for 72 hours, and the resulting reaction was monitored by HPLC. At the point in time when no change was seen in the HPLC chart (after 30 hours or later), the reaction was completed. In this HPLC, 5C18-AR-II Waters 4.6×250 mm was used as a column, 38 to 50% by mass of water (0.1% by mass of TFA) (solvent A) or 38 to 50% by mass of acetonitrile (0.1% by mass of TFA) (solvent B) was flowed as an elution solvent at a flow rate of 1.0 mL/min. for 30 minutes, and the detection was carried out at a detection wavelength of 220 nm.

Figure 25:
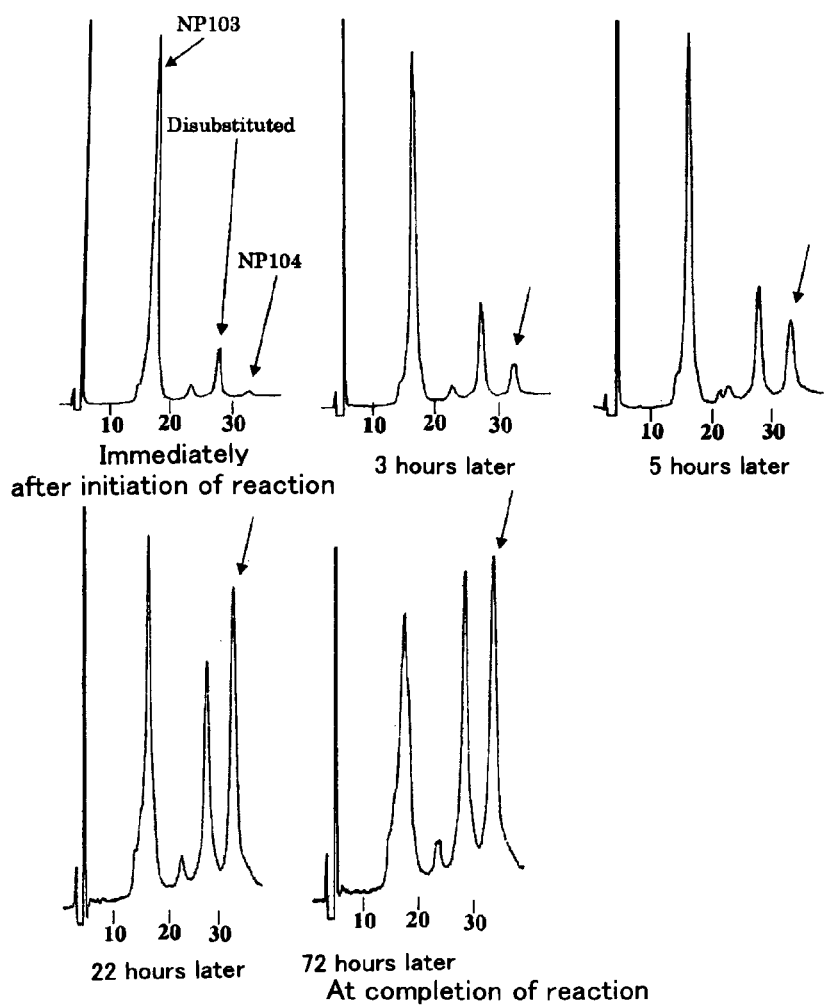
FIG. 25 is a diagram showing an HPLC chart obtained by monitoring the synthesis reaction of NP104.
Figure 26:
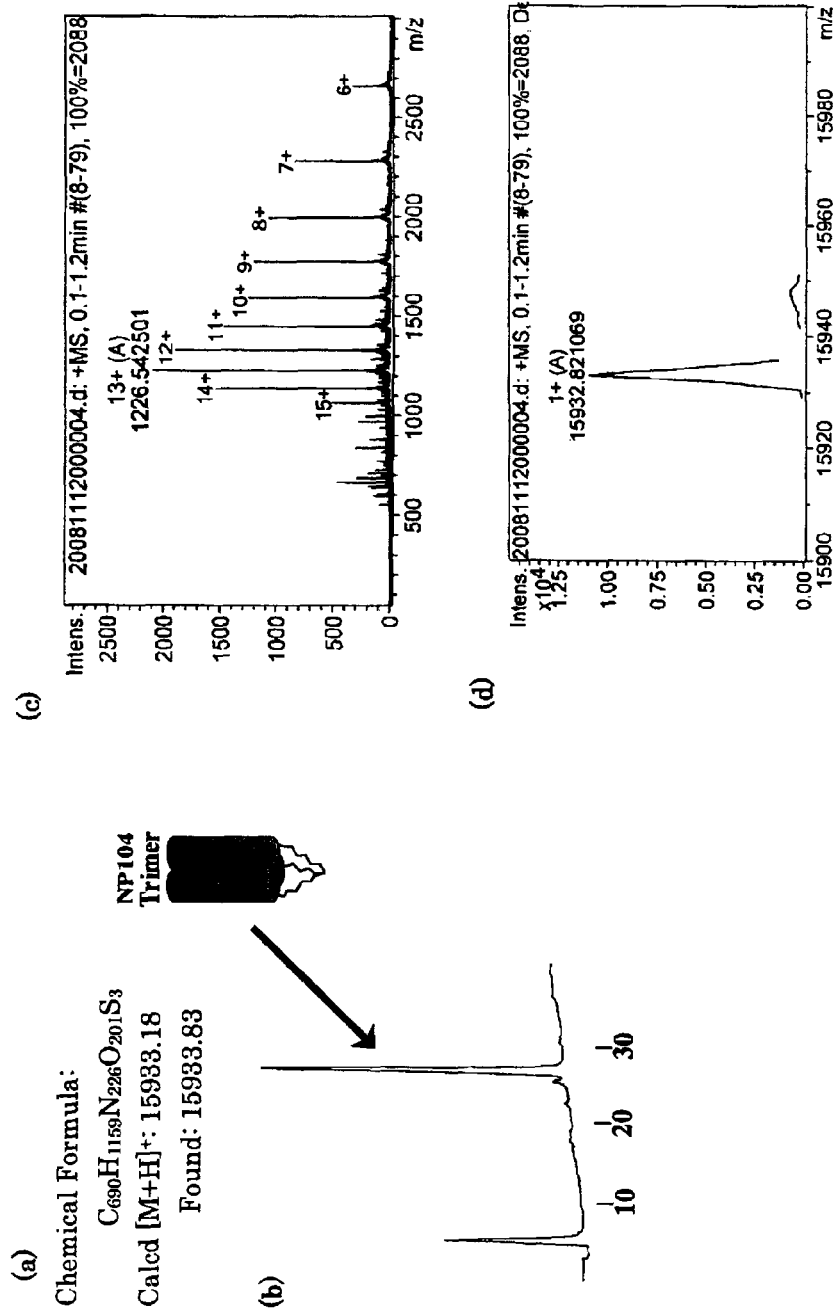
FIG. 26 is a diagram related to the synthesis of NP104.

Results of the HPLC chart are shown in FIG. 25. A fraction corresponding to each peak in this HPLC chart was collected, and the fraction in a solution was purified by RP-HPLC (column: YMC-Pack ODS-A, 10ϕ×250 mm) and then analyzed by ESI-TOF-MS. The results of this ESI-TOF-MS are shown in FIG. 26. The results of this ESI-TOF-MS could demonstrate that: the peak obtained at HPLC RT (retention time) of 16.4 minutes represented the NP103 monomer; the peak obtained at RT of 28.1 minutes represented two molecules of NP103 ligated to the template compound; and the peak obtained at RT of 34.2 minutes represented NP104, the compound of interest (FIG. 27). As a result, it was also confirmed that the reaction occurred specifically for the N-terminal cysteine residue of NP103. When the reaction time was made longer to further promote the reaction, compounds formed by the hydrolysis of the ester moiety could be confirmed by ESI-TOF-MS. Thus, it was concluded that the reaction would no longer proceed. Then, NP104 was purified. Specifically, a fraction (solution) corresponding to the peak corresponding to NP104 was collected and further purified using a linear gradient of 40 to 50% by mass for 50 minutes or longer in the solvent B to obtain NP104 (yield: 16%). The identification data of this NP104 is as follows:

ESI-TOF-MS, m/z calcd for $C_{690}H_{1160}N_{226}O_{201}S_3$ 15933.1. found 15933.8.

(5) Measurement of CD Spectra

It has previously been reported that N36 assumes α-helix as a secondary structure. To confirm whether NP102 (monomer) and NP104 (trimer) thus synthesized respectively assumed such an α-helix structure and the difference between their structures, circular dichroism (CD) spectra were measured. This is because the measurement of CD spectra permits easy prediction of the presence or absence of secondary structures of proteins or their types and contents. Specifically, proteins rich in α-helix are known to exhibit positive peaks around 190 nm and negative peaks at 208 and 222 nm. Proteins rich in β-structure are known to often have positive peaks at 195 to 200 nm and negative peaks around 215 nm. Proteins containing a random coil structure are known to have negative peaks around 200 nm.

Conditions for the measurement of CD spectra involved measurement in 20 mM acetate buffer (pH 4.0) containing 40% methanol which was considered to be useful as a model of environments similar to the surroundings of biomembranes. The measurement conditions are based on the idea that protein denaturation is induced by the synergistic effect of moderate decrease in pH and decrease in permittivity in the surroundings of biomembranes, and are considered to be optimal for assaying the trimeric structure synthesized in this study (Bychkova, V. E., Dujsekina, A. E., Klenin, S. I., Ptisyn O. B. Molten globule-like state of cytochrome c under conditions simulating those near the membrane surface. Biochemistry 35, 6058-6063 (1996); Nishi, N., Komine, Y., Sakai, N., Maruyama, T., Otagiri, M. cooperative effect of hydrophobic and electrostatic forces on alchol-induced α-helix formation of $α_1$-acid glycoprotein. FEBS Lett. 579, 3596-3600 (2005)). The N36 peptide derivative synthesized in this study contained only one tryptophan (T). From previous studies, it is known that this tryptophan is positioned on a solution side even in the trimer formation. Thus, NP102 (monomer) and NP104 (trimer) concentrations were calculated from the absorbance of this tryptophan. For this purpose, the molar absorption coefficient of tryptophan was first measured using this measurement solution. The concentration of tryptophan contained in NP102 (monomer) and NP104 (trimer) synthesized this time was calculated using the value of the molar absorption coefficient of tryptophan, and the concentrations of NP102 and NP104 in assay samples were corrected. The concentration correction was performed such that NP104 (trimer) had 1/3 of the concentration of NP102 (monomer) to equalize the concentrations of the N36 monomers. Specifically, the concentration of NP102 was set to 10 μM; thus the concentration of NP104 was set to 10/3 μM. CD spectra for the concentration-corrected NP102 and NP104 assay samples were respectively measured at 25° C. at a scanning rate of 100 nm/min. with a time constant of 1 s and a resolution of 0.1 nm in a quartz cell having an optical path length of 1.0 mm using J720 spectropolarimeter equipped with a thermostat. The results are shown in FIG. 28. As is evident from FIG. 28, both the NP102 and NP104 assay samples exhibited spectra characteristic of α-helix, i.e., the positive maximum around 190 nm and the negative maximum at 208 nm and 222 nm, showing that both the samples were rich in α-helix.

Based on the CD spectra of FIG. 28, the helix contents of NP102 and NP104 were determined. The following equations were both used as equations for determining the helix contents based on previous reports (Chen, Y.-H., Yang, J. T., Chau, K. H. Determination of the helix and beta form of proteins in aqueous solution by circular dichroism. Biochemistry 13, 3350-3359 (1974); Gan, P. J., Lyu, P. C., Manning, M. C., Woody, R. W., Kallendach, N. R. The helix-coil transition in heterogeneous peptides with specific side-chain interactions: theory and comparison with CD spectral data. Biopolymers 31, 1605-1614 (1991); Jackson, D. Y., Hing, D. S., Chmieleski, J., Singh, S., Schultz, P. G. General approach to the synthesis of short α-helical peptides. J. Am. Chem. Soc. 113, 9391-9392 (1991)).

$$[\theta]_{max} = [\theta]_\infty (1 - k/n)$$

$$\text{Helix content (\%)} = [\theta]_{222}/[\theta]_{max} \times 100$$

In both the equations, $[\theta]_\infty$ represents −41000, which is the molar ellipticity of infinite helix, k represents 4.3, which is an empirically determined constant; and n represents the number of amino acid residues. As a result of calculating the α-helix contents of NP102 and NP104 using both the equations, they were 73% and 95%, respectively, showing that NP104 had a larger α-helix content than that of NP102 (FIG. 29). Furthermore, from previous studies, it is known that a peptide assumes a coiled-coil structure when the value of $[\theta]_{222}/[\theta]_{208}$ is larger than 1. The value of $[\theta]_{222}/[\theta]_{208}$ was 0.96 for NP104, which was closer to 1 than that for NP102. Thus, NP104 seems to assume a coiled-coil structure when assuming a trimeric structure. This is also consistent with results of previously performed experiments on gp41 (Non-Patent Documents 10 to 12). The experimental results described above also demonstrated that the synthesized NP104 was the trimer of the N36 peptide derivative of interest.

Example 2

Immunization with Trimer of N36 Peptide Derivative and Evaluation of Serum (1) Immunization with NP102 (Monomer) and NP104 (Trimer)

The experiments of Reference Example 2 described above could demonstrate that the animal experimental system using mice and the serum evaluation system functioned. Thus, the antibody induction experiment of Reference Example 2 was conducted on NP102 (monomer) synthesized in the paragraph (2) of Example 1 and NP104 (trimer) synthesized in the paragraph (4) of Example 1.

First, mice were immunized with NP102 or NP104. The dose of the antigen molecule used in the immunization of the mice and the immunization schedule followed the method described in Reference Example 2. Specifically, the immunization was performed by a method shown below. A solution for immunization was prepared by mixing 1.0 µL of DMSO (endotoxin-free) (manufactured by Sigma-Aldrich Corp.) containing 100 µg of synthetic peptide, 50 µL of PBS (manufactured by Wako Pure Chemical Industries, Ltd.), and 50 µL of Freund's incomplete adjuvant (manufactured by Wako Pure Chemical Industries, Ltd.). Each mouse anesthetized with diethyl ether was placed in a supine position and immunized by the subcutaneous injection of the solution for immunization containing the positive control, the negative control, NP102, or NP104. The immunization was repeated five times at 1-week intervals for all the mice.

For the timing of collection of blood, the collection of blood was started 3 weeks after the first immunization for the antibody titer evaluation in Reference Example 2. However, in this experiment, a sufficient rise in antibody titer was already seen 3 weeks after the first immunization. Thus, blood was collected at 1-week intervals from a lapse of 1 week from the first immunization. The schedule of immunization and collection of blood in this experiment is shown in FIG. 30. The number of the immunized mice was set to 3 per sample, and the mice were numbered for differentiation. These three mice were differentiated for immunization such that: the mouse from which the right ear was excised was indicated in "right"; the mouse from which the left ear was excised was indicated in "left"; and the mouse free from such excision of the ears was indicated in "both". In this context, the collection of blood was performed from the orbital floor. The collected blood was separated into serum and clot by centrifugation at 15000 rpm at 4° C. for 15 minutes. The obtained serum was inactivated at 56° C., then centrifuged again, and used as a serum sample. This serum was stored at −80° C., and used by thawing when used in the subsequent experiment.

(2) Evaluation of Serum by ELISA

The ELISA method constructed in Reference Example 2 was used to evaluate antibodies contained in the serum of each mouse immunized with NP102 or NP104. First, the verification was conducted that antibodies contained in the mouse serum obtained with the negative control did not recognize NP102 or NP104. The results are shown in FIG. 31. As shown in FIG. 31, it was demonstrated that the serum of the mouse that received the negative control did not recognize NP102 (FIG. 31(a)) or NP104 (FIG. 31(b)). Subsequently, the verification was conducted that antibodies in the serum of the mouse immunized with the positive control, NP102, or NP104 recognized the corresponding antigen molecule. The results are shown in FIG. 32. As shown in FIG. 32, it was confirmed that the antibody titer in each sample gradually rose with increase in the number of lapsed days. Specifically, NP102-recognizing antibodies, were induced in the serum of the mouse immunized with NP102 (FIG. 32(a)). NP104-recognizing antibodies were induced in the serum of the mouse immunized with NP104 (FIG. 32(b)). Positive control-recognizing antibodies were induced in the serum of the mouse immunized with the positive control (FIG. 32(c)).

(3) Confirmation of Specificity of Antibody

To confirm that antibodies contained in serum of each mouse immunized with NP102 (monomeric N36 peptide derivative) or NP104 (trimer of the N36 peptide derivative) specifically recognized the corresponding antigen molecule, an antigen molecule different from the antigen molecule used in the immunization was immobilized onto a microplate, and the antibody titer of antibodies in the serum was evaluated. Specifically, the experiment was conducted by a method shown below.

Each mouse was immunized with NP102 or NP104 at 1-week intervals. Then, blood was collected at 1-week intervals from the first week of immunization, and the obtained serum was evaluated by ELISA. FIG. 33(a) shows results of evaluating antibodies in the serum of the mouse immunized with NP102, using the NP104-immobilized microplate; and FIG. 33(b) shows results of evaluating antibodies in the serum of the mouse immunized with NP104, using the NP102-immobilized microplate. As shown in FIG. 33, an antibody titer was not detected until a serum dilution of approximately $10^{-2}$, depending on the timing of collection of blood. The antibody titer confirmed in FIG. 33 was considerably low, compared with FIG. 32 in which the antibody titer was detected even at a serum dilution on the order of $10^{-4}$ to $10^{-3}$. This suggested that the antibodies contained in the serum obtained by immunization with NP102 or NP104 were sufficiently specific for the antigen molecule (NP102 or NP104) used in the immunization. Moreover, both NP102 and NP104 were N36 peptide derivatives and had the same amino acid sequence, strongly suggesting that the antibodies contained in the serum obtained by immunization with NP104 specifically recognized and bound to the three-dimensional structure of NP104.

Example 3

Evaluation on Anti-HIV Activity of Trimer of N36 Peptide Derivative (NP104)-1-(p24 Assay)

(1) Preparation of HIV-1 Virus Solution

To confirm whether NP104 had an anti-HIV activity, p24 assay was conducted. p24 is a capsid protein constituting the core of HIV-1. It is known that when HIV multiplies in an organism infected with HIV, p24 concentrations rise in the serum of the organism. For the p24 assay, HIV-1 virus was first prepared. Specifically, a method shown below was used.

An HIV-1 molecular clone pNL4-3 (clade B; X4-tropic virus) was prepared. Next, 293T cells were added to a Petri dish of 10 cm in diameter containing 10% FBS/DMEM (Wako Pure Chemical Industries, Ltd.) and cultured until they became 60% confluent. These cultured 293T cells were transfected with 10 μg of pNL4-3 using Lipofectamine LTX (manufactured by Invitrogen Corp.). 6 to 12 hours after the transfection, the culture solution was replaced with 10% FBS/RPMI1640 (manufactured by Wako Pure Chemical Industries, Ltd.). Then, the cells were cultured for 24 to 48 hours under conditions involving 37° C. and a carbon dioxide concentration of 5% by mass. A supernatant was collected from the obtained culture solution. This supernatant was filtered through a filter of 0.45 μm in pore size, and the filtrate was used as a virus solution.

This virus solution was rapidly cooled using liquid nitrogen and then stored at −80° C. or lower until use.

(2) Measurement of Infectivity Titer of Virus Solution

The infectivity titer of the virus solution prepared in the paragraph (1) of Example 3 was measured. Specifically, the measurement was performed by a method shown below. First, the virus solution prepared in the paragraph (1) of Example 3 was diluted 10-fold with 10% FBS/RPMI1640. The diluted virus solution was added to each well of a 96-well plate. Further, serial dilution series of 2-fold or 3-fold dilutions (11 rows of wells; the 12th row of wells was used as a blank) were prepared. All the volumes of the dilution series were adjusted to 100 μL. On the other hand, MT-4 cells (T-cell lineage) cultured in 10% FBS/RPMI1640 were added at a concentration of $10^4$ cells/100 μL/well to the wells of the dilution series and cultured. On the 3rd day of culture, the culture solution (100 μL) was gradually replaced so as not to change the number of cells in each well. After culture for 4 days from the replacement, a culture supernatant was collected from the culture solution. The amount of HIV-1 p24 was measured, and the viral titer (the number of viruses/mL) was determined from a dilution factor at which the p24 value was 0. This numeric value was corrected using a measurement value of the amount of HIV-1 p24 in a culture solution obtained by directly culturing the dilution series of the virus solution without the addition of MT-4 cells as a background.

(3) Confirmation of Anti-HIV Effect (HIV Infection Inhibitory Effect)

To confirm whether serum containing induced IgG specific for the NP104 antigen had an HIV infection inhibitory effect, the following procedures were performed: first, each serum obtained in Example 2 was added in the predetermined amount to wells of each 24-well plate. To these wells, MT-4 cells were inoculated at a concentration of $5 \times 10^4$ cells/well (4 times or 9 times the volume of the serum) and pretreated for 1 hour. After the pretreatment, the pNL4-3 virus solution prepared in the paragraphs (1) and (2) of Reference Example 2 was added at M.O.I.=0.05 to 0.01 for viral infection. Also, wells containing only MT-4 cells and the pNL4-3 virus solution without the addition of serum were prepared as a background. After lapses of 3, 5, and 7 days from the viral infection, a supernatant in each well was collected, and the expression level of p24 was measured by ELISA related to HIV-1 p24. As a result, it was confirmed that the serum obtained by immunization with NP104 had the HIV infection inhibitory effect. Moreover, after a lapse of 3 days from the viral infection, the solution in the wells was centrifuged to collect cells, which were then subjected to Western blot analysis related to p24. Moreover, a negative control (nega) collected from wells containing only MT-4 cells and the pNL4-3 virus solution without the addition of serum was also subjected to Western blot analysis in the same way as above. The results of these Western blot analyses are shown in FIG. 34. As is evident from FIG. 34, no reduction in the amount of p24 was seen in any samples obtained using the serum obtained by immunization with the N36 monomer NP102, showing that, the samples did not have the HIV infection inhibitory effect (see "M-3" and "M-2"). By contrast, when the serum obtained by immunization with the N36 peptide trimer NP104 was used, no reduction in the amount of p24 was seen in "T-3" which exhibited a lower antibody titer for NP104. However, the amount of p24 was significantly reduced in "T-2" having a higher antibody titer for NP104, demonstrating that this sample exhibited the HIV infection inhibitory effect.

Example 4

Evaluation on Anti-HIV Activity of N36 Peptide Trimer (NP104)-2-(MTT Assay)

NP102 (monomer), NP104 (trimer), and an HIV drug AZT (3'-azido-3'-deoxythymidine) known in the art were evaluated for their anti-HIV activities using MTT assay (Org. Biomol. Chem., 2008, 6, 4374-4377), a method known in the art. The results are shown in the left panel of FIG. 35. Moreover, these 3 kinds of samples were evaluated for their cytotoxicities. The results are shown in the right panel of FIG. 35. Based on these results, $EC_{50}$ (μM) and $CC_{50}$ (μM) of the anti-HIV activity were calculated, and the results are shown in the lower panel of FIG. 35. As is evident from these results, NP104 (trimer) having approximately ⅓ of the concentration of NP102 (monomer) was shown to exert the anti-HIV activity equivalent to that of NP102 (monomer) and to have approximately 1/10 of the cytotoxicity of NP102. This demonstrated that NP104 trimerized using the template compound of the present invention was structurally similar to the N36 trimer of the native gp41 protein and the NP104-recognizing antibody actually had the anti-HIV activity.

INDUSTRIAL APPLICABILITY

According to a method for synthesizing a peptide antigen inducing an HIV three-dimensional structure-recognizing antibody according to the present invention, a "trimer of N36 peptide derivative" that mimics the native three-dimensional structure can be obtained using a monomeric N36 peptide as the monomeric peptide of interest and a template compound. Therefore, the application of the synthesis method of the present invention to various fields is expected. For example, a peptide trimer comprising a template compound ligated to a derivative of a peptide (monomer) constituting a type I viral fusion protein, such as an HIV N36 peptide, has an inhibitory activity on viral (particularly, HIV) invasion into a cell and as such, is particularly useful in the field of preventive or therapeutic agents for viral (particularly, HIV) infection.

The invention claimed is:

1. A peptide antigen capable of inducing an HIV three-dimensional structure-recognizing antibody that recognizes a trimer region of a N-terminal helical region of an HIV particle transmembrane protein gp41 (N36), wherein the peptide antigen comprises: a trimer of N36 peptide derivatives comprising three N36 peptide derivatives ligated to a C3-symmetric template compound having three equivalent linker structures, wherein each N36 peptide derivatives comprises SEQ ID NO: 1; and wherein the C3-symmetric template compound having three equivalent linker structures is the compound of formula (1):

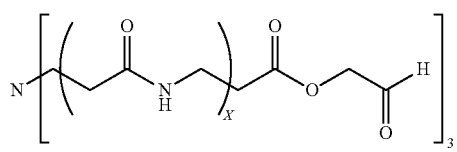

(wherein X represents a positive integer).

2. The peptide antigen according to claim 1, wherein the N36 peptide derivative is synthesized by a solid-phase synthesis method using selective deprotection of a 9-fluorenylmethoxycarbonyl (Fmoc) group and a condensation reaction.

3. The peptide antigen according to claim 1, wherein the N36 peptide derivative is obtained by introducing a Cys to the N-terminus of the N36 peptide and introducing one residue of Gly as a spacer between the N36 peptide sequence and the Cys.

4. The peptide antigen according to claim 1, wherein the C3-symmetric template compound having three equivalent linker structures is the compound of formula (2):

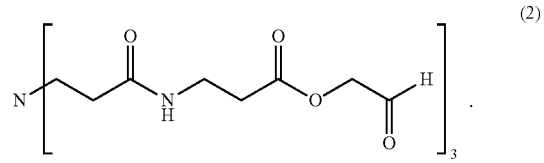

5. The peptide antigen according to claim 1, wherein the N36 peptide derivative is obtained by adding a total of 6 residues of hydrophilic amino acids Arg and Glu to the N terminus of the N36 peptide, and further placing Cys at the N terminus thereof, and placing Gly as a spacer between the Cys and Arg.

6. The peptide antigen according to claim 5, wherein the N36 peptide derivative is a compound of formula (3):

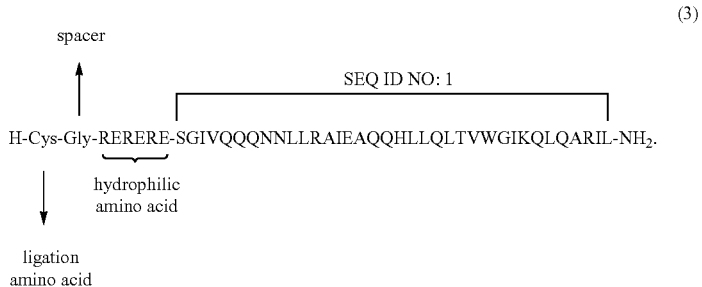

7. The peptide antigen according to claim 1, wherein synthesizing the trimer of the N36 peptide derivative involves stirring the C3-symmetric template compound having three equivalent linker structures and the N36 peptide derivative with an acetate buffer to thereby ligate the N36 peptide derivative to the C3-symmetric template compound having three equivalent linker structures.

8. A method of inducing an immune response to HIV comprising administering to a subject the peptide antigen according to claim 1.

* * * * *

SEQUENCE LISTING

<160> NUMBER OF SEQ ID NOS: 1

<210> SEQ ID NO 1
<211> LENGTH: 36
<212> TYPE: PRT

```
<213> ORGANISM: Artificial sequence
<220> FEATURE:
<223> OTHER INFORMATION: N36 peptide
<220> FEATURE:
<223> OTHER INFORMATION: Inventor:Tamamura, Hirokazu; Nakahara, Toru;
      Nomura, Wataru

<400> SEQUENCE: 1

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
            35
```